US008556865B2

(12) United States Patent
Krulevitch et al.

(10) Patent No.: US 8,556,865 B2
(45) Date of Patent: Oct. 15, 2013

(54) MEDICAL MODULE FOR DRUG DELIVERY PEN

(75) Inventors: Peter Krulevitch, Pleasanton, CA (US); Robert Wilk, Sierra Village, CA (US); Ulrich Kraft, Hofheim (DE); Donna Savage, Rolling Hills Estates, CA (US); Nick Foley, Edinburgh (GB); James Glencross, Edinburgh (GB); David Shepherd, Edinburgh (GB); Zara Sieh, San Ramon, CA (US)

(73) Assignee: LifeScan, Inc.

( * ) Notice: Subject to any disclaimer, the term of this patent is extended or adjusted under 35 U.S.C. 154(b) by 0 days.

(21) Appl. No.: 13/203,691

(22) PCT Filed: Jan. 27, 2010

(86) PCT No.: PCT/US2010/022236
§ 371 (c)(1),
(2), (4) Date: Sep. 8, 2011

(87) PCT Pub. No.: WO2010/098927
PCT Pub. Date: Sep. 2, 2010

(65) Prior Publication Data
US 2011/0313349 A1 Dec. 22, 2011

Related U.S. Application Data

(60) Provisional application No. 61/156,386, filed on Feb. 27, 2009, provisional application No. 61/156,421, filed on Feb. 27, 2009, provisional application No. 61/156,472, filed on Feb. 27, 2009, provisional application No. 61/164,250, filed on Mar. 27, 2009.

(51) Int. Cl.
*A61M 5/315* (2006.01)
*A61M 5/178* (2006.01)
*A61M 5/00* (2006.01)

(52) U.S. Cl.
USPC ............ 604/223; 604/227; 604/186; 604/246

(58) Field of Classification Search
USPC ......... 604/207–211, 223–224, 227–228, 181, 604/218, 186, 246, 65–76
See application file for complete search history.

(56) References Cited

U.S. PATENT DOCUMENTS 4,803,625 A 2/1989 Fu et al.
4,950,246 A 8/1990 Muller
(Continued)

FOREIGN PATENT DOCUMENTS

EP 1363224 A1 11/2003
WO WO 99/043283 A1 9/1999
(Continued)

OTHER PUBLICATIONS

M. Franetzki, et al., "Design and Data of a Compact Device for Sustained Program-Controlled Medicament Infusion" Hormone and Metabolic Research, Supplement Series (1982), 12 (Islet-Pancreas-Transplant. Artif. Pancreas), 169-172, ISSN: 0170-5903, ISBN: 086577062x.

(Continued)

*Primary Examiner* — Nicholas Lucchesi
*Assistant Examiner* — Rebecca E Eisenberg

(57) ABSTRACT

Various embodiments of a medical module are provided which includes a primary module housing, a secondary module housing, a dosage sensor, a power source, and a microcontroller. The module is configured to be attached to a disposable drug delivery pen or a reusable drug delivery pen so that the module may: determine dosage selected, injection of selected dosage, duration of injection, time of injection, whether the pen has been primed or shaken to thoroughly mix up insulin mixtures, transmit information relating to insulin dosage and injection to a data management unit, provide reminders, error warning or messages on improper usage or reuse of needles, track amount of drug remaining on board the pen or duration of usage of pen with respect to expiry of the drug on board, or provide an audible alarm for locating misplaced pen and module.

26 Claims, 16 Drawing Sheets

(56) References Cited

U.S. PATENT DOCUMENTS

| | | | |
|---|---|---|---|
| 4,995,402 A | 2/1991 | Smith et al. | |
| 5,204,670 A | 4/1993 | Stinton | |
| 5,216,597 A | 6/1993 | Beckers | |
| 5,383,865 A | 1/1995 | Michael | |
| 5,417,222 A | 5/1995 | Dempsey et al. | |
| 5,536,249 A | 7/1996 | Castellano et al. | |
| 5,558,638 A | 9/1996 | Evers et al. | |
| 5,593,390 A | 1/1997 | Castellano et al. | |
| 5,611,784 A * | 3/1997 | Barresi et al. | 604/211 |
| 5,678,562 A | 10/1997 | Sellers | |
| 5,728,074 A | 3/1998 | Castellano et al. | |
| 5,820,602 A | 10/1998 | Kovelman et al. | |
| 5,830,152 A | 11/1998 | Tao | |
| 5,925,021 A | 7/1999 | Castellano et al. | |
| 5,950,632 A | 9/1999 | Reber et al. | |
| 5,957,896 A | 9/1999 | Bendek et al. | |
| 6,024,699 A | 2/2000 | Surwit et al. | |
| 6,038,676 A | 3/2000 | Yanes et al. | |
| 6,134,504 A | 10/2000 | Douglas et al. | |
| 6,144,922 A | 11/2000 | Douglas et al. | |
| 6,192,891 B1 | 2/2001 | Gravel et al. | |
| 6,235,004 B1 | 5/2001 | Steenfeldt-Jensen et al. | |
| 6,270,455 B1 | 8/2001 | Brown | |
| 6,277,099 B1 | 8/2001 | Strowe et al. | |
| 6,298,017 B1 | 10/2001 | Kulakowski et al. | |
| 6,443,890 B1 | 9/2002 | Schulze et al. | |
| 6,482,185 B1 | 11/2002 | Hartmann | |
| 6,524,239 B1 | 2/2003 | Reed et al. | |
| 6,540,672 B1 | 4/2003 | Simonsen et al. | |
| 6,554,798 B1 | 4/2003 | Mann et al. | |
| 6,585,698 B1 | 7/2003 | Packman et al. | |
| 6,641,533 B2 | 11/2003 | Causey, III et al. | |
| 6,790,178 B1 | 9/2004 | Mault et al. | |
| 6,817,986 B2 | 11/2004 | Slate et al. | |
| 6,869,413 B2 | 3/2005 | Langley et al. | |
| 6,942,646 B2 | 9/2005 | Langley et al. | |
| 7,169,132 B2 | 1/2007 | Bendek et al. | |
| 7,397,730 B2 | 7/2008 | Skyggebjerg et al. | |
| 7,427,275 B2 | 9/2008 | DeRuntz et al. | |
| 7,713,229 B2 | 5/2010 | Veit et al. | |
| 2002/0052578 A1 | 5/2002 | Moller | |
| 2002/0126036 A1 | 9/2002 | Flaherty et al. | |
| 2003/0005891 A1 | 1/2003 | Lu | |
| 2003/0023203 A1 | 1/2003 | Lavi et al. | |
| 2003/0038047 A1 | 2/2003 | Sleva et al. | |
| 2003/0208113 A1 | 11/2003 | Mault et al. | |
| 2003/0220814 A1 | 11/2003 | Gordon | |
| 2004/0122355 A1 | 6/2004 | Langley et al. | |
| 2005/0049179 A1 | 3/2005 | Davidson et al. | |
| 2005/0182358 A1 | 8/2005 | Veit et al. | |
| 2006/0153693 A1 | 7/2006 | Fiechter et al. | |
| 2006/0173260 A1 * | 8/2006 | Gaoni et al. | 600/365 |
| 2006/0224123 A1 | 10/2006 | Friedli et al. | |
| 2007/0021715 A1 | 1/2007 | Kohlbrenner et al. | |
| 2007/0060800 A1 | 3/2007 | Drinan et al. | |
| 2007/0123829 A1 | 5/2007 | Atterbury et al. | |
| 2007/0129708 A1 | 6/2007 | Edwards et al. | |
| 2008/0099366 A1 | 5/2008 | Niemiec et al. | |
| 2008/0188813 A1 | 8/2008 | Miller et al. | |
| 2008/0208142 A1 | 8/2008 | Moller | |
| 2008/0306434 A1 | 12/2008 | Dobbles et al. | |
| 2008/0312605 A1 | 12/2008 | Saiki | |
| 2009/0012479 A1 | 1/2009 | Moller et al. | |
| 2009/0163793 A1 | 6/2009 | Koehler et al. | |
| 2010/0286665 A1 * | 11/2010 | Manna et al. | 604/542 |
| 2010/0292635 A1 * | 11/2010 | Sundar | 604/67 |

FOREIGN PATENT DOCUMENTS

| | | |
|---|---|---|
| WO | WO 02/062212 A3 | 8/2002 |
| WO | WO 03/005891 A1 | 1/2003 |
| WO | WO 03/047426 A1 | 6/2003 |
| WO | WO 2004/006785 A1 | 1/2004 |
| WO | WO 2006/075016 A1 | 7/2006 |

OTHER PUBLICATIONS

Lord, et al., "MiniMed Technologies Programmable Implantable Infusion Sysyem," Annals of the New York Academy of Sciences, 1988;531:66-71.

Prestele, et al., "A Remote-Programmable Implantable Insulin Dosing Device Part 1" Techincal Concept and Features, Hormone and Metabolic Research, Supplement Series (1982), 12 (Islet-Pancreas-Transplant. Artif. Pancreas), 304-7, ISSN: 0170-5903, ISBN: 086577062x.

Christopher D. Saudek, "Development of Implantable Insulin Infusion Devices", Methods in Diabetes Research, vol. II: Clinical Methods, 1986, pp. 347-360, Editors Clarke, William; Larner, Joseph; et al.

HumaPen Memoir (revised Nov. 20, 2006) (retrieved from http://pi.lilly.com/us/memoir_user_manual.pdf accessed on Mar. 15, 2010).

The Smart Pen by John Walsh, May 18, 2008 (retrieved from http://challengediabetes.diabetech.net/2008/05/14the-smart-insulin-pen-by-john-walsh/ accessed on Mar. 15, 2010).

The Smart Pen by John Walsh, (retrieved from http://www.diabetesnet.com/diabetes_technology/smart_pen.php accessed on Mar. 15, 2010).

Chinese Patent Application No. 201080019326.9, Chinese First Office Action dated Feb. 6, 2013, 6 pages, State Intellectual Property Office, P.R. China.

European Patent Application No. 10746603.9, extended European search report dated Jan. 10, 2013, 8 pages, European Patent Office, Germany.

* cited by examiner

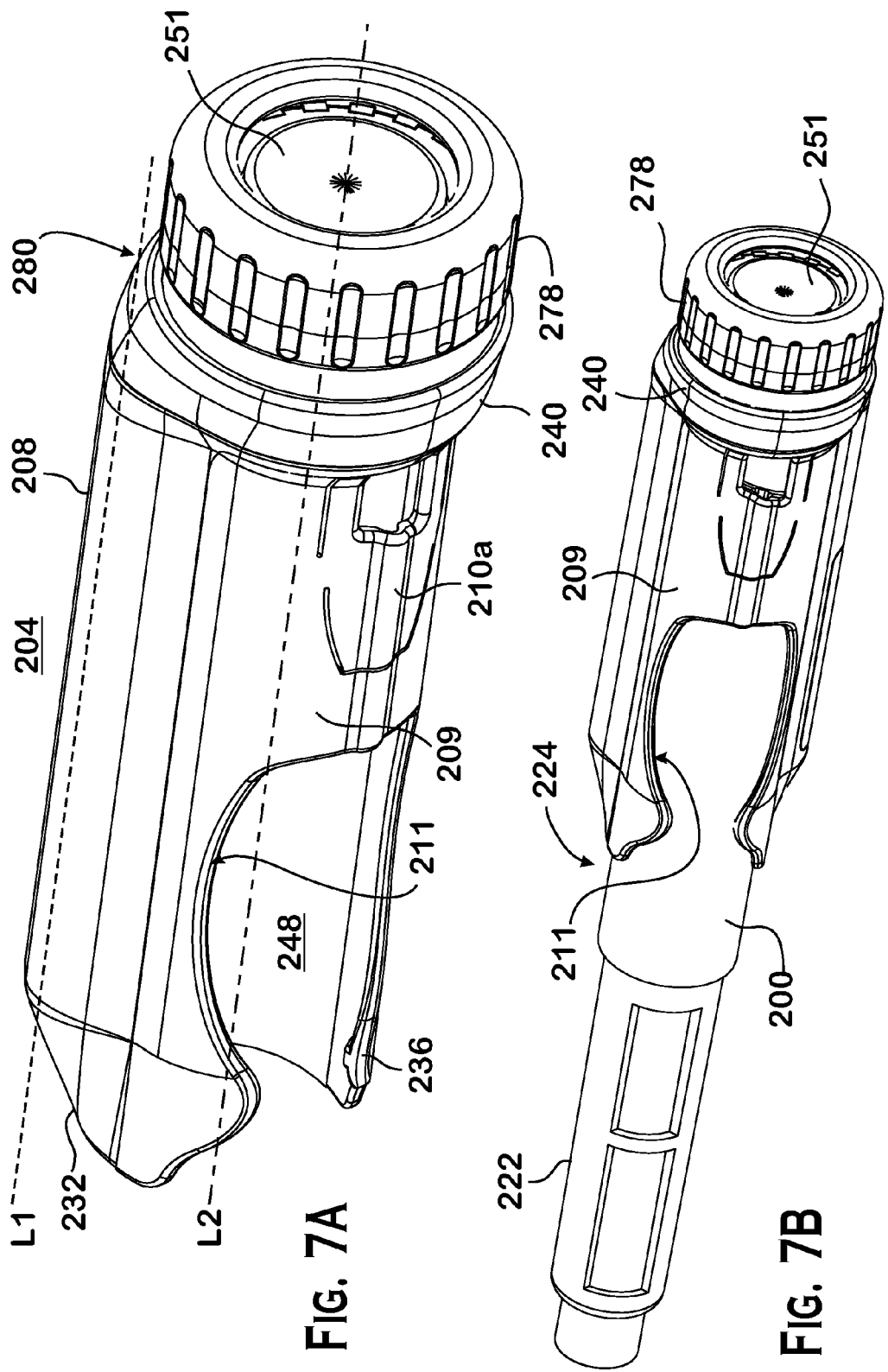

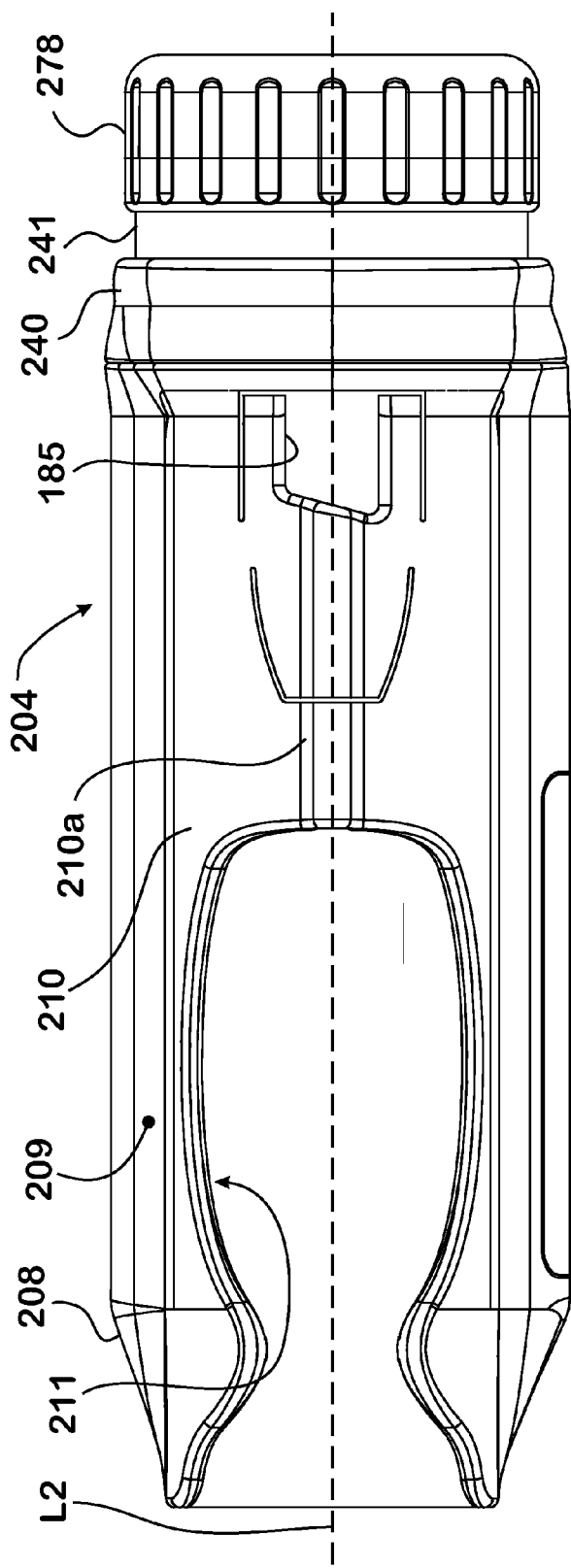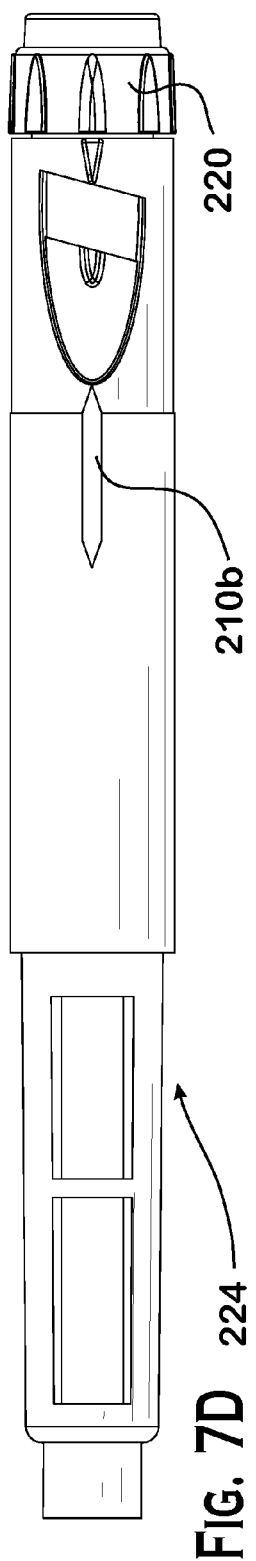
FIG. 7C
FIG. 7D

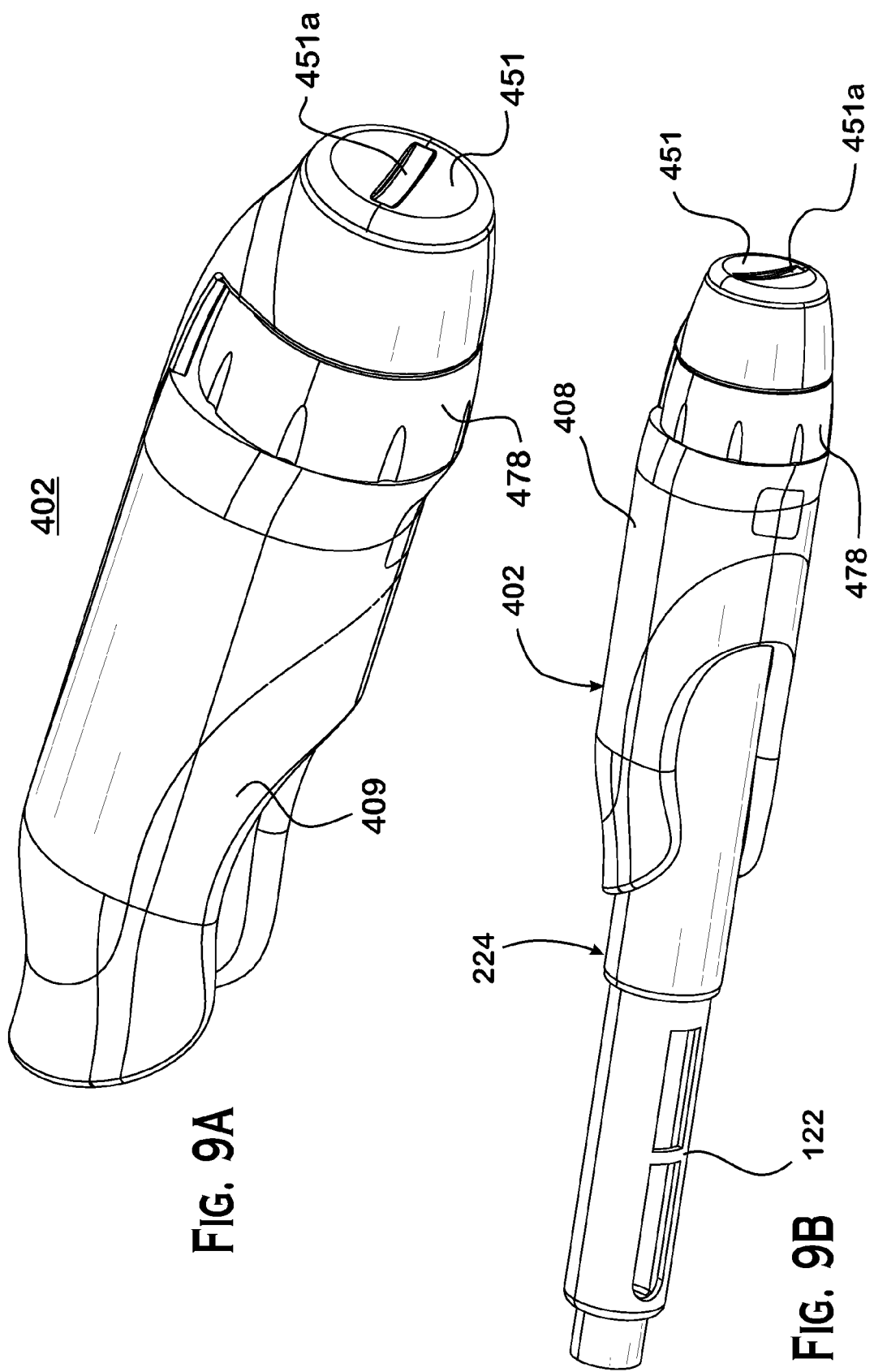

MEDICAL MODULE FOR DRUG DELIVERY PEN

PRIORITY

This application claims the benefits of priority under 35 USC §§120 and 371 of International Application No. PCT/US2010/022236, filed Jan. 27, 2010, which claims the benefit of priority under 35 USC §119 to Provisional Patent Application Ser. No. 61/156,386, filed on Feb. 27, 2009, entitled "Medical Module for Drug Delivery Pen"; International Application No. PCT/US2010/022241, filed Jan. 27, 2010, which claims the benefit of priority under 35 USC §119 to Provisional Patent Application Ser. No. 61/156,421, filed on Feb. 27, 2009, entitled "Drug Delivery System"; International Application No. PCT/US2010/022242, filed Jan. 27, 2010, which claims the benefit of priority under 35 USC §119 to Provisional Patent Application Ser. No. 61/156,472 filed on Feb. 27, 2009, entitled "Drug Delivery Management Systems and Methods"; International Application No. PCT/US2010/022245, filed Jan. 27, 2010, which claims the benefit of priority under 35 USC §119 to Provisional Patent Application Ser. No. 61/164,250 filed on Mar. 27, 2009, entitled "DRUG DELIVERY MANAGEMENT SYSTEMS AND METHODS", all of which are incorporated by reference in their entirety herein.

BACKGROUND

It is believed that five million people worldwide, or approximately 56% of all insulin users, use insulin pens to inject their insulin. Insulin pens are convenient, easy to use, and discrete compared to syringes and vials, resulting in improved adherence and better outcomes. In addition, insulin pens reduce the time required for health care practitioners to initiate insulin therapy.

SUMMARY OF THE DISCLOSURE

Embodiments of the present invention address key issues, including: bringing together insulin therapy and blood glucose monitoring into more integrated therapeutic/monitoring systems; simplifying insulin initiation and intensification protocols; making blood glucose values central in the management of diabetes; and providing diabetes system solutions for improved outcomes and lower costs. The embodiments of the present invention help the patient and care provider stay on top of insulin therapy by automatically communicating delivered doses to a blood glucose meter, by recording the amount and time of insulin delivery, and by displaying a summary of a patient's blood glucose and insulin administration history. The embodiments of the present invention confirm whether the patient has already dosed, keeps track of the time and amount of insulin delivery, and eliminates the need to keep a manual logbook. Embodiments of the present invention help health care practitioners keep track of patient compliance.

Not only will embodiments of the invention facilitate management of diabetes, the invention and its embodiments will also be applicable in any field where drug delivery to a patient is utilized. For example, in the field of pain management or arthritis management, anxiety or epilepsy management (e.g., Diazepam) and the like.

In view of the foregoing and in accordance with one aspect of the present invention, there is provided a medical module that includes a primary module housing, a secondary module housing, a dosage sensor, a power source, and a microcontroller. The module housing extends along a first longitudinal axis from a first module housing end to a second module housing end. The secondary module housing is coupled to the casing module and extends along a second axis to define a hollow bore, which hollow bore is configured for attachment over an actuation unit of a drug delivery pen. The dosage sensor is coupled to the primary module housing, while the power source is coupled to the primary module housing and is spaced apart from the dosage sensor. The microcontroller is disposed in the primary module housing and is coupled to both the dosage sensor and the power source.

In yet a further aspect, the secondary module housing includes first and second extensions that partially circumscribe the second longitudinal axis generally parallel to the first longitudinal axis.

In yet a further aspect, each of the first and second extensions includes respective first and second locating tangs, which protrude beyond each extension.

In yet a further aspect, the first locating tang is located at a position along the second longitudinal axis offset longitudinally with respect to the second locating tang.

In yet a further aspect, each of the first and second extensions defines a generally circular cross-section of generally 30 degrees about the second longitudinal axis.

In yet a further aspect, a portion of the secondary module housing circumscribes the second longitudinal axis to define a generally circular cross-section of generally 140 degrees about the longitudinal axis.

In yet a further aspect, a portion of the secondary module housing is contiguous to both the first and second extensions, defining a continuous surface that circumscribes generally 250 degrees about the second axis.

In yet a further aspect, the dosage sensor includes a longitudinal member slidable along the longitudinal axis. The longitudinal member is connected to a follower portion that extends from the primary module housing proximate the second module housing end.

In yet a further aspect, the longitudinal member is configured for rotation about its axis.

In yet a further aspect, the secondary module housing includes a generally tubular extension circumscribing entirely the second longitudinal axis and defining a hollow bore that extends along a length of the module housing.

In yet a further aspect, the microcontroller includes: a memory; a microprocessor coupled to the memory; an analog-to-digital converter coupled to the dosage sensor and the microprocessor so as to provide data on displacement of the follower portion; and a transmitter to transmit data stored in the memory.

In yet a further aspect, the drug delivery pen includes a disposable insulin pen.

In yet a further aspect, the drug delivery pen includes a reusable insulin pen.

In yet a further aspect, the dosage sensor is selected from a group consisting of a rotary potentiometer, linear potentiometer, capacitive displacement sensor, optical displacement sensor, magnetic displacement sensor, encoder type displacement sensor, or combination thereof.

In yet a further aspect, an inertial sensor is disposed in the module housing to determine the orientation of the drug delivery pen.

In yet a further aspect, a micro switch is disposed in the module housing to allow determination of replacement of the drug delivery pen.

In another aspect of the present invention, there is provided a medical communication unit that includes a housing, dosage sensor, knob, and micro-controller. The housing extends along a longitudinal axis from a first housing end to a second housing end to define at least a portion of a hollow bore in which the hollow bore is configured to couple over an actuation unit of a drug delivery pen. The dosage sensor is coupled to the housing and offset to the longitudinal axis. The knob is mounted to the housing and coupled to the dosage sensor. The micro-controller is disposed proximate the housing and the dosage sensor.

In yet a further aspect, a medical communication unit is provided that includes a housing, means for measuring displacement of a drug delivery pen, and means for determining one of a dosage delivery or duration of the dosage delivery of a drug delivery pen. The housing extends along a longitudinal axis from a first housing end to a second housing end to define at least a portion of a hollow bore in which the hollow bore is configured to couple over an actuation unit of a drug delivery pen.

These and other embodiments, features and advantages will become apparent when taken with reference to the following more detailed description of the embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred exemplary embodiments of the invention, and, together with the general description given above and the detailed description given below, serve to explain features of the invention (wherein like numerals represent like elements), of which:

FIG. 7A illustrates a perspective view of a third medical unit.

FIG. 7B illustrates a perspective view of the medical unit mounted to yet another drug delivery device.

FIG. 7C illustrates a plan view of the unit of FIG. 7A.

FIG. 7D illustrates a plan view of the drug delivery device of FIG. 7B.

FIG. 9A illustrates a perspective view of yet another type of medical module by itself.

FIG. 9B illustrates a perspective view of the module of FIG. 9A as coupled to a drug delivery pen.

DETAILED DESCRIPTION OF THE FIGURES

Figure 1:
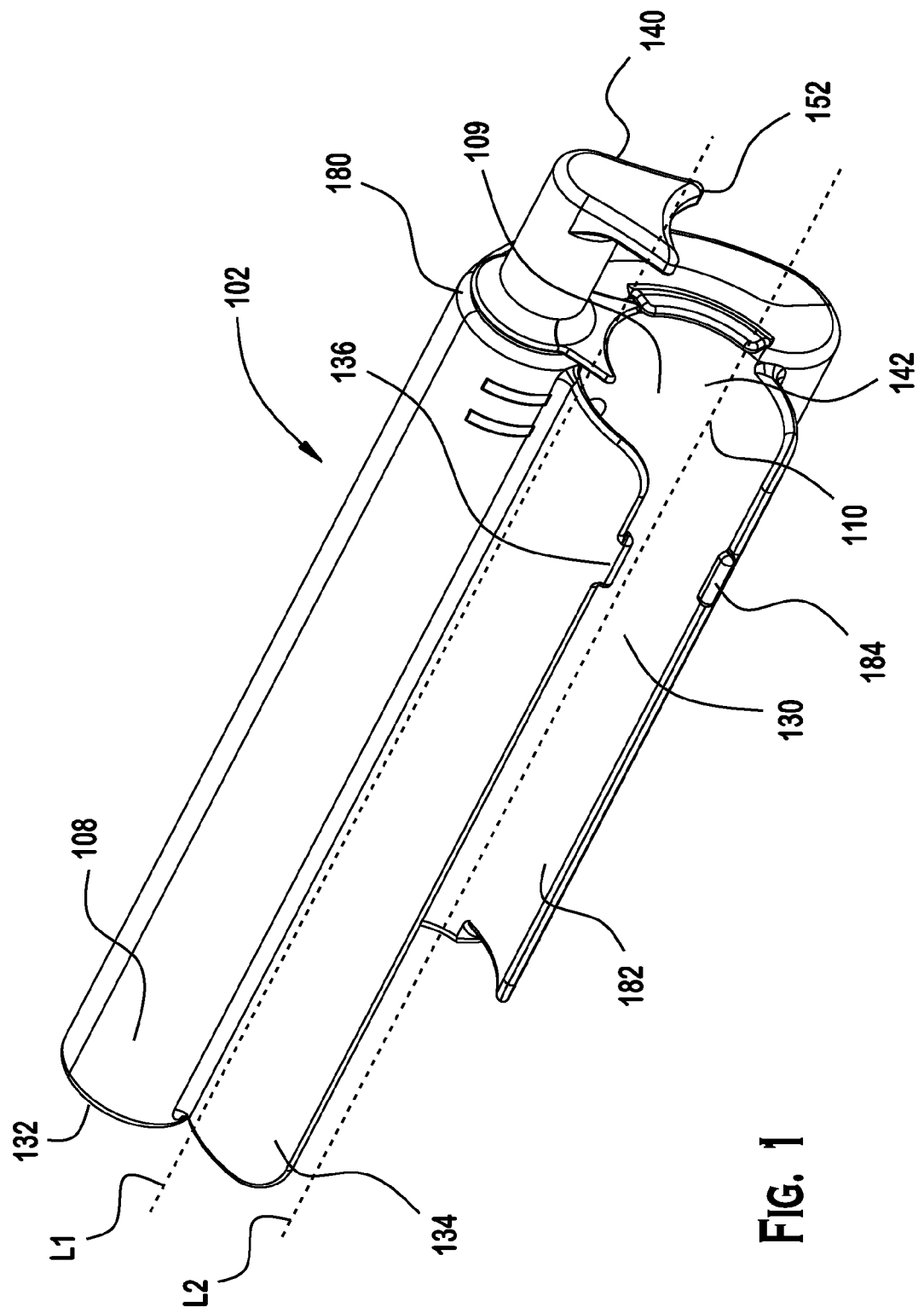
FIG. 1 illustrates a front perspective view of a first type of medical module, according to an exemplary embodiment described and illustrated herein.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Insulin pens are commonly used as a simple, convenient, and effective technique for delivering insulin. Unlike syringes, which must be filled from a vial and require the user to estimate the dose volume based on the position of a meniscus against a fine graduated scale, insulin pens are accurate and relatively easy to use. Insulin pens come in two basic types: (1) disposable pens that come pre-loaded with the insulin cartridge and are thrown away after the cartridge is empty, and (2) re-usable pens that require the user to load the insulin cartridges. Most insulin pens are purely mechanical, but there are versions on the market that have digital displays and record the most recent dosing history in memory (see, for example, the Humapen Memoir). To use a pen, the user attaches a needle, primes the device, dials in the desired dose, inserts the needle subcutaneously, and then presses a button to inject.

Despite the simplicity and ease of use of insulin pens relative to syringes, applicants have recognized that there are aspects that may be improved. For example, applicants note that the typical disposable pens do not record insulin delivery events. This makes it difficult for the patient and their doctor to retrospectively analyze insulin delivery patterns and the relationship with blood glucose data. This is necessary to help the user and their doctor understand the relationship between blood glucose levels and insulin delivery in order to optimize insulin dosing. In addition, patients who have forgotten whether or not they have taken their insulin have no way to verify a delivery event. A missed injection may result in hyperglycemia (two missed bolus shots per week is known to raise HbA1C levels), and taking too much insulin could result in a life-threatening hypoglycemic event. While models such as the Humapen Memoir record the most recent injections in the pen memory, the insulin industry in some countries is moving away from durable pens in favor of disposables. In the pens that store data, it is not possible to download long-term data to study it in conjunction with blood glucose data. While others have speculated on so-called "smart pen" devices that incorporate wireless communication, for example "the Smart Insulin Pen" by John Walsh, P. A., C.D.E. (see, for example, http://www.diabetesnet.com/diabetes_technology/smart-_pen.php), these are complex devices that are not consistent with the disposable pen model being adopted by the insulin companies. Finally, the regulatory pathway for approval of new pen devices is a long and expensive process.

Recognizing the shortcomings of the conventional insulin pens, applicants have invented various embodiments of a medical module that may be used not only with conventional insulin pens but also with any drug delivery pen. Various exemplary embodiments of the medical module are provided with useful features. For example, the modules are provided with dose sensing and wireless communication capabilities. The unit may be designed to work with various disposable drug delivery pens manufactured by the different insulin companies. The unit may be used in conjunction with pen devices for delivering medications other than insulin, such as, for example, growth hormone, GLP-1 analogs, Symlin, biologic molecules, and other injected biopharmaceuticals.

In the exemplary embodiments, the medical module is preferably a small, low profile, lightweight device that attaches to a disposable or reusable drug delivery device (e.g., an insulin pen) and measures the amount of drug (e.g., insulin) that is injected. The size and weight of such unit make it acceptable to carry the device attached to the pen in a pocket or purse, in the same way a user would carry a stand-alone pen. Preferably, the device does not impede normal functions of the drug delivery device, including turning the dosing dial, viewing the selected dose in the dose window, and pressing on the injection button to deliver a dose. After attaching the medical module, it does not add more steps to the process of using a drug delivery device during typical injections. The unit also records the amount of drug, such as, for example, insulin and date and time of the injection in memory, and may transmit the data to a data management unit for review by healthcare practitioners. In one preferred embodiment, the data management unit may include a paired analyte meter (e.g., a glucose meter which may be a non-continuous glucose meter or continuous glucose sensing meter) that receives or transmits data when the two devices are in range of each other. In such embodiment, the meter (not shown) keeps track of the drug dosing history, along with analyte (e.g., blood glucose values) for retrospective analysis by the patient and HCP. The device helps patients remember if they have taken their prescribed drug such as, for example, insulin, and may reduce the number of missed boluses, a key factor influencing HbA1c. The device also has several features that guide the user in the proper use of the drug delivery device, improving accuracy and reducing the burden of the HCP to train patients on insulin pen therapy. While the exemplary embodiments utilize a glucose sensor meter in the form of a data management unit, other types of analyte sensors may be used in conjunction with the module for the delivery of the appropriate injectable fluids such as, for example, growth hormone, GLP-1 analogs, Symlin, biologic molecules, and other injectable biopharmaceuticals.

First Type of Medical Module

As shown in FIG. 1, the exemplary module 102 includes a housing 108 that extends along longitudinal axis L1 from a first end 132 to a second end 180 to define at least a portion 142 of a hollow bore 109. The hollow bore 109 is adapted to be coupled to a drug delivery pen in one operative mode and to be separated from the pen in another operative mode. Upon separation from the pen, the module is no longer coupled to the actuation mechanism of the pen and in fact is lacking in an actuation mechanism, e.g., a plunger, push rod, or the like, such that an internal surface of the hollow bore is exposed to the ambient environment so as to be visible to an ordinary observer or user. Portion 142 is configured for attachment over an actuation unit 100 of a drug delivery device 124 or 224 (e.g., an insulin pen), shown here in FIGS. 3 and 6B. Housing 108 includes a first and second extension portions 130 and 134 that circumscribes about second axis L2 to define at least a portion of a hollow bore 109, locator tangs 136 and 184 (which are offset longitudinal with respect to each other along axis L2, dosage sensor 114, locator forks 152a and 152b with follower portion 140 that may reciprocate longitudinally along a longitudinal axis L1. The follower portion 140 is physically or directly connected to the dosage sensor 114. In one embodiment, each of extensions 130 and 134 extends in a generally circular path about axis L2 of about 30 degrees. Where greater security of engagement between the extensions and the pen is needed, each of extensions 130 and 130 may be increased to define any ranges from generally 30 degrees to generally 250 degrees (or even 360 degrees to provide for a continuous bore as illustrated in FIG. 8) about axis L2.

Figure 2:
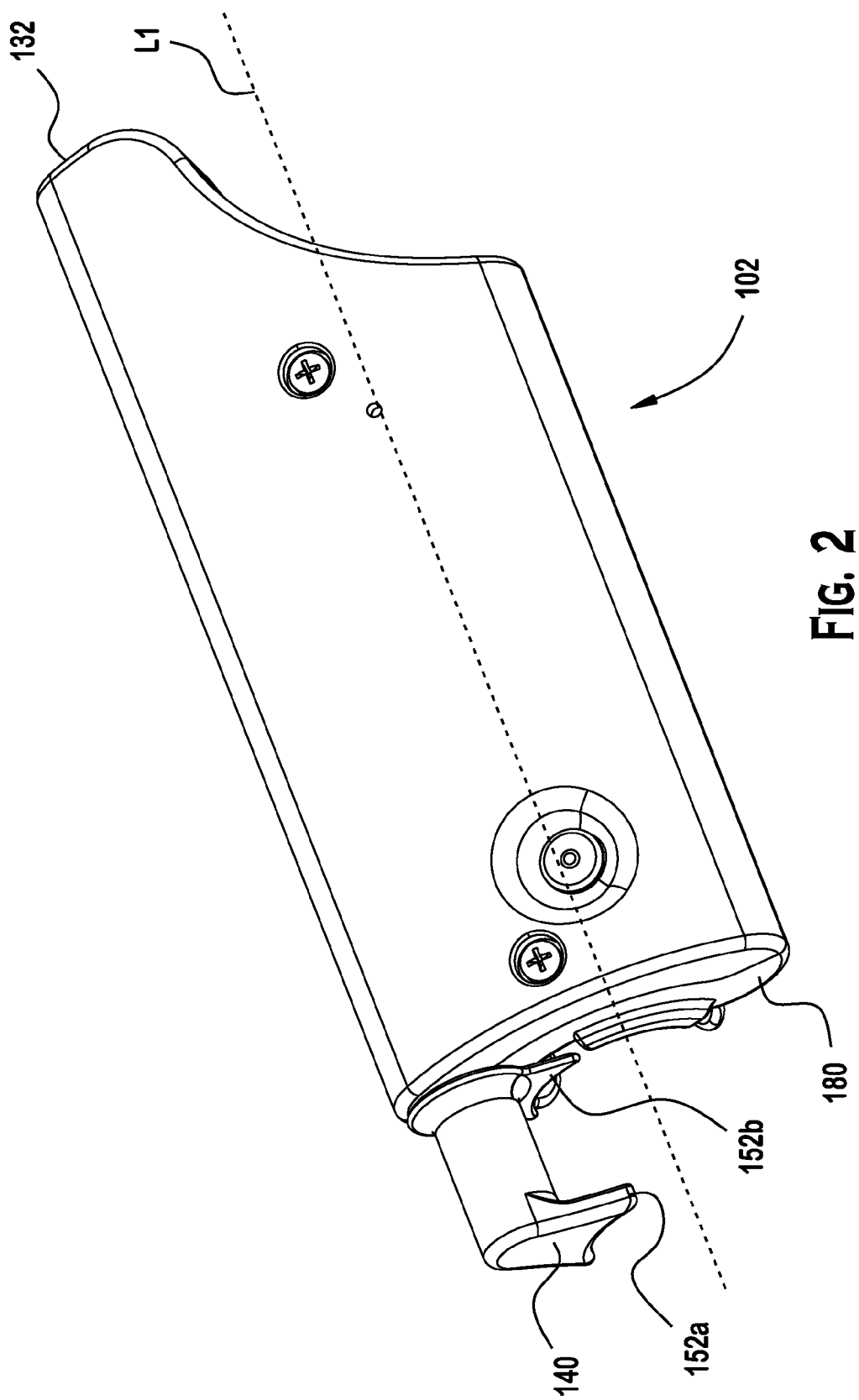
FIG. 2 illustrates a rear perspective view of the medical module, according to an exemplary embodiment described and illustrated herein.
Figure 3:
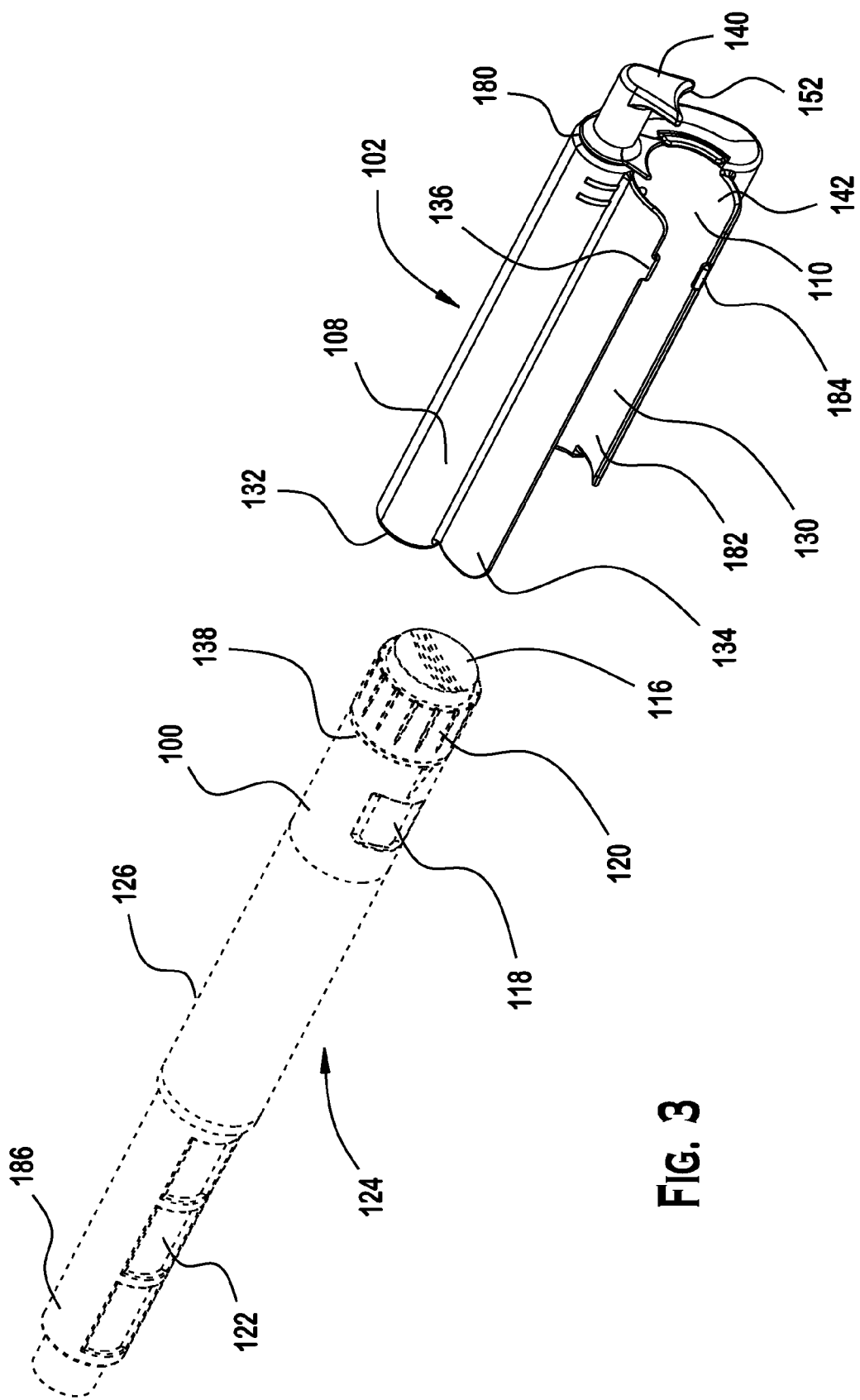
FIG. 3 illustrates a perspective view of the medical module and a drug delivery pen, according to an exemplary embodiment described and illustrated herein.

FIG. 2 shows the back of the module 102 illustrated in FIG. 1. FIG. 3 illustrates module 102 as part of a conventional drug delivery pen prior to assembly of the two components.

Figure 5:
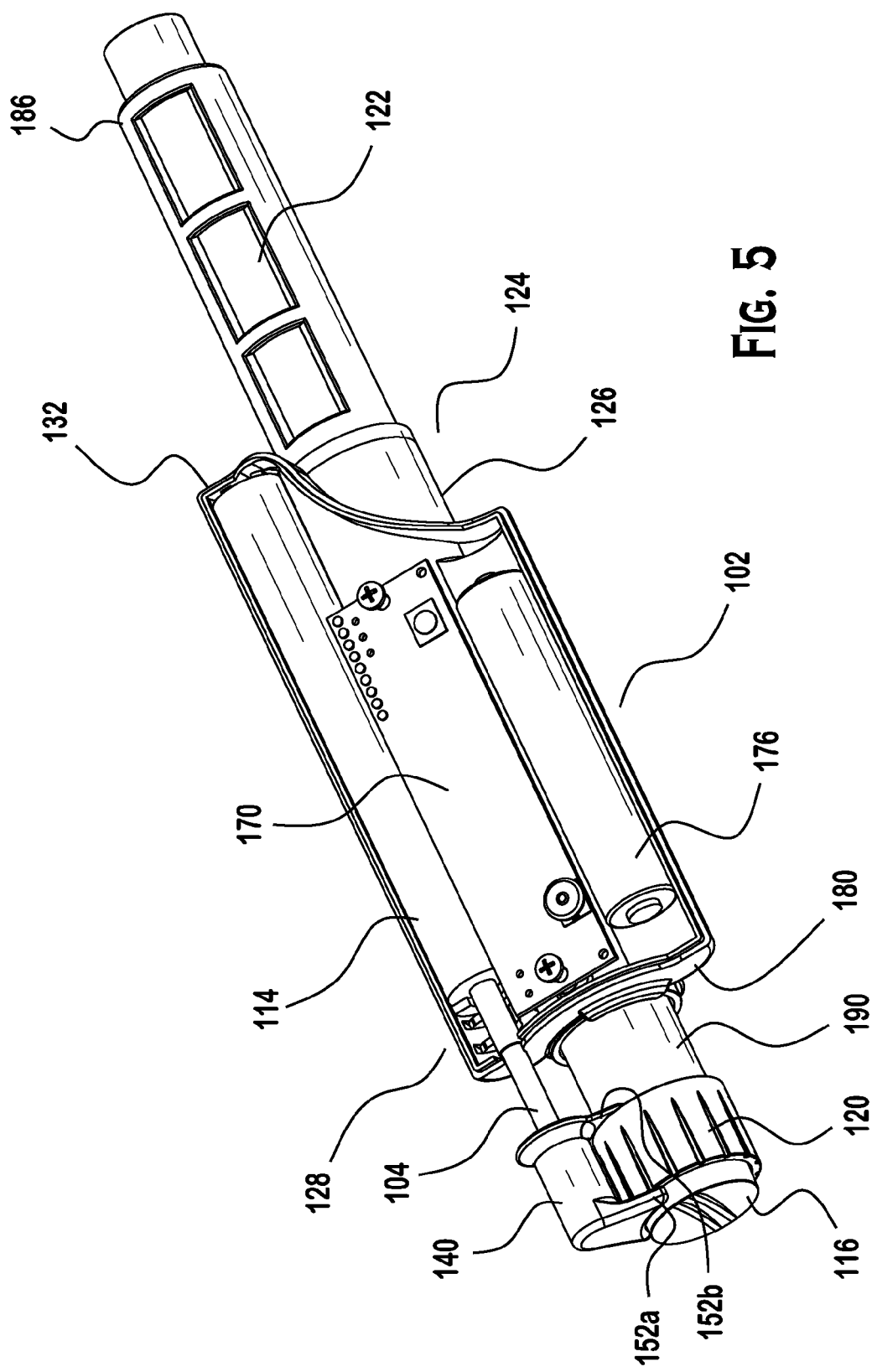
FIG. 5 illustrates a rear perspective view of FIG. 4, where the rear cover of the medical module has been removed, according to an exemplary embodiment described and illustrated herein.

Referring to FIG. 1, follower portion 140 is configured to be physically connected directly to sensor 114 and permitted to rotate about its own axis. A power source 176 is also provided in a location preferably spaced apart from dosage sensor 114 (FIG. 5). A microcontroller, depicted here as controller board 170 in FIG. 5, is coupled to both sensor 114 and power source 176 to allow for a determination of position, movements or even direction of movement of a dosage selector 120 (see FIGS. 2 and 3).

Figure 4:
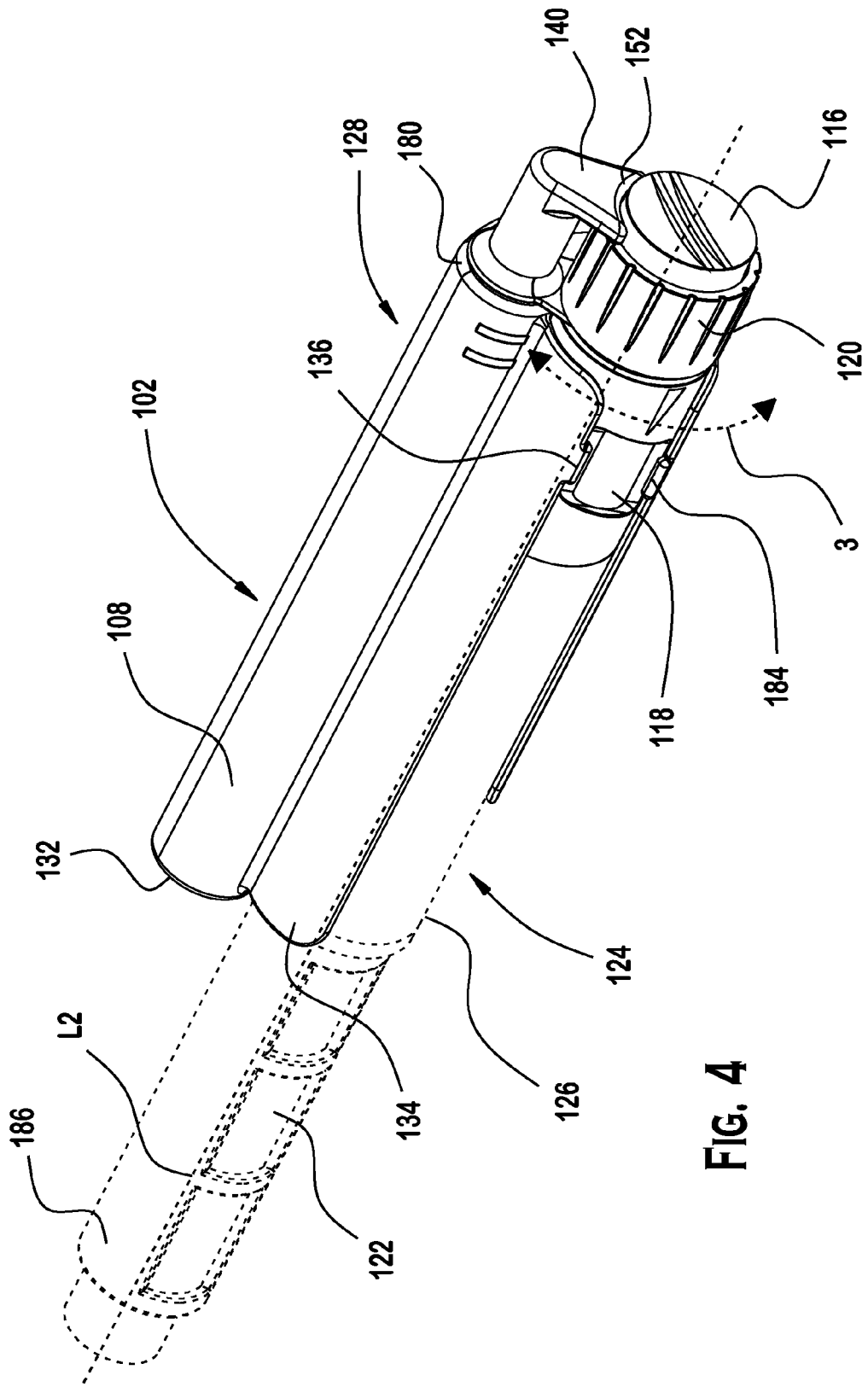
FIG. 4 illustrates a perspective view of the medical module and a drug delivery pen, where the medical module has been attached to the drug delivery pen, according to an exemplary embodiment described and illustrated herein.

FIG. 4 shows locator tabs 136 and 184 for aligning module 102 with dose display window 118 of the pen. Locator tabs 136 and 184 align snap-on unit 102 with drug delivery device 124 and prevent unit 102 from rotating and obscuring dose display window 118 of drug delivery device 124. For module 102, extensions 134 and 182, with locating tangs 136 and 184, allow module 102 to snap on over pen 124. After inserting drug delivery pen 124, locating tangs 136 and 184 engage dosage indicator window 118, securing medical module 102 to drug delivery pen 124. Dosage selector 120 engages follower portion 140, allowing dosage selector 120 to move along its axis as dosage is adjusted. Extensions 134 and 182 leave an opening through which the user may view dosage indicator window 118 and labeling on the drug delivery pen 124. As shown in FIG. 5, locator forks 152a and 152b are coupled to dosage selector 120 such that follower portion 140 follows the axial movement of dosage selector 120 (which itself is rotational to allow for axial motion of dosage selector) or delivery button 116 (which is axial).

FIG. 5 shows module 102 with the top housing removed to reveal the internal components. In particular, FIG. 5 shows the location of longitudinal member 154 and locator forks 152a and 152b prior to injection with follower 154 extended to a selected dosage. Module 102 includes housing 108, battery 176, microprocessor circuit board 170, dosage sensor 114, and longitudinal member 154. Dosage sensor 114 is used to measure the injected dose. Longitudinal member 154 moves parallel to the longitudinal axis L2 of the pen, tracking with dosage selector 120 as it moves in and out with actuation shaft 190 of drug delivery pen 102. Electrical circuit components (not shown due to placement of components in the drawings) are provided on board 170 such as, for example, microprocessor, microcontroller, analog-to-digital converter, speaker, display, memory, display driver, user interface driver, transmitter, receiver or transmitter-receiver (e.g., a wireless transceiver using infrared light, radio-frequency, or optical waves) and antenna to send and receive wireless signals to and from the meter, process input from the sensor, turn the device on and off, put the device into sleep mode, wake the device up, regulate power from battery 176, and store and retrieve information to and from memory, as examples. Dosage sensor 114 is preferably a linear potentiometer and is used to measure the position of dosage selector 120 for determining the size of the bolus injected by the user. Sensor 114 is electrically coupled to an analog-to-digital converter, which is coupled to microprocessor board 170 to provide data on the position of dosage selector 120 and dosage actuator 116. A micro-switch is provided at a position proximate housing end 132 to provide an indication of drug delivery upon button 116 being fully depressed to push shaft 190 towards cartridge 122. Other sensors that may be used with the exemplary embodiments include rotational potentiometers, linear, or rotational encoders. Linear potentiometers are preferred in the operational prototypes built by applicants. However, the embodiments described herein may utilize means for determining displacement of a dosage selector of a drug delivery pen in which the means include a follower, longitudinal member, and a dosage sensor (which may include rotary potentiometer, linear potentiometer, capacitive displacement sensor, optical displacement sensor, magnetic displacement sensor, encoder type displacement sensor, or combinations and equivalents thereof) and equivalents to these components described herein. In the embodiment of FIG. 1, the drug delivery pen may be a NovoLog® Flex-Pen manufactured by Novo Nordisk.

Second Type of Module

Recognizing that different drug delivery devices (e.g., insulin pens) may require alternative coupling technique, applicants have provided for an alternative that is designed to be inserted over one end of drug delivery device 124 or 224 rather than being attached from the side as in the prior embodiment. As with the first module type, a hollow bore of the module is adapted to be coupled to a drug delivery pen in one operative mode and to be separated from the pen in another operative mode. Upon separation from the pen, the module is no longer coupled to the actuation mechanism of the pen and in fact is lacking in an actuation mechanism, e.g., a plunger, push rod, or the like, such that an internal surface of the hollow bore is exposed to the ambient environment so as to be visible to an ordinary observer or user.

Figure 6A:
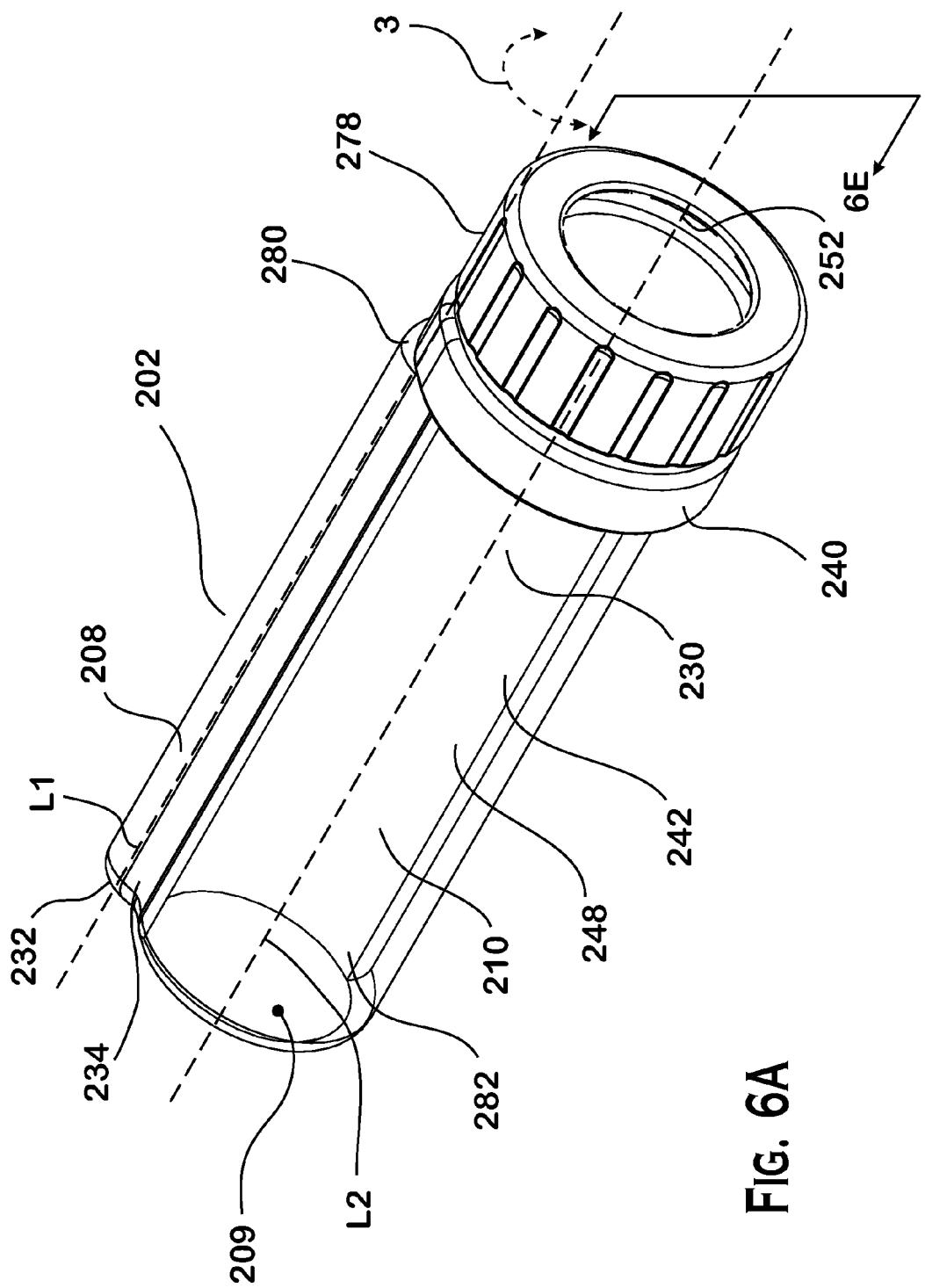
FIG. 6A illustrates a front perspective view of a second type of medical module, according to an exemplary embodiment described and illustrated herein.
Figure 6B:
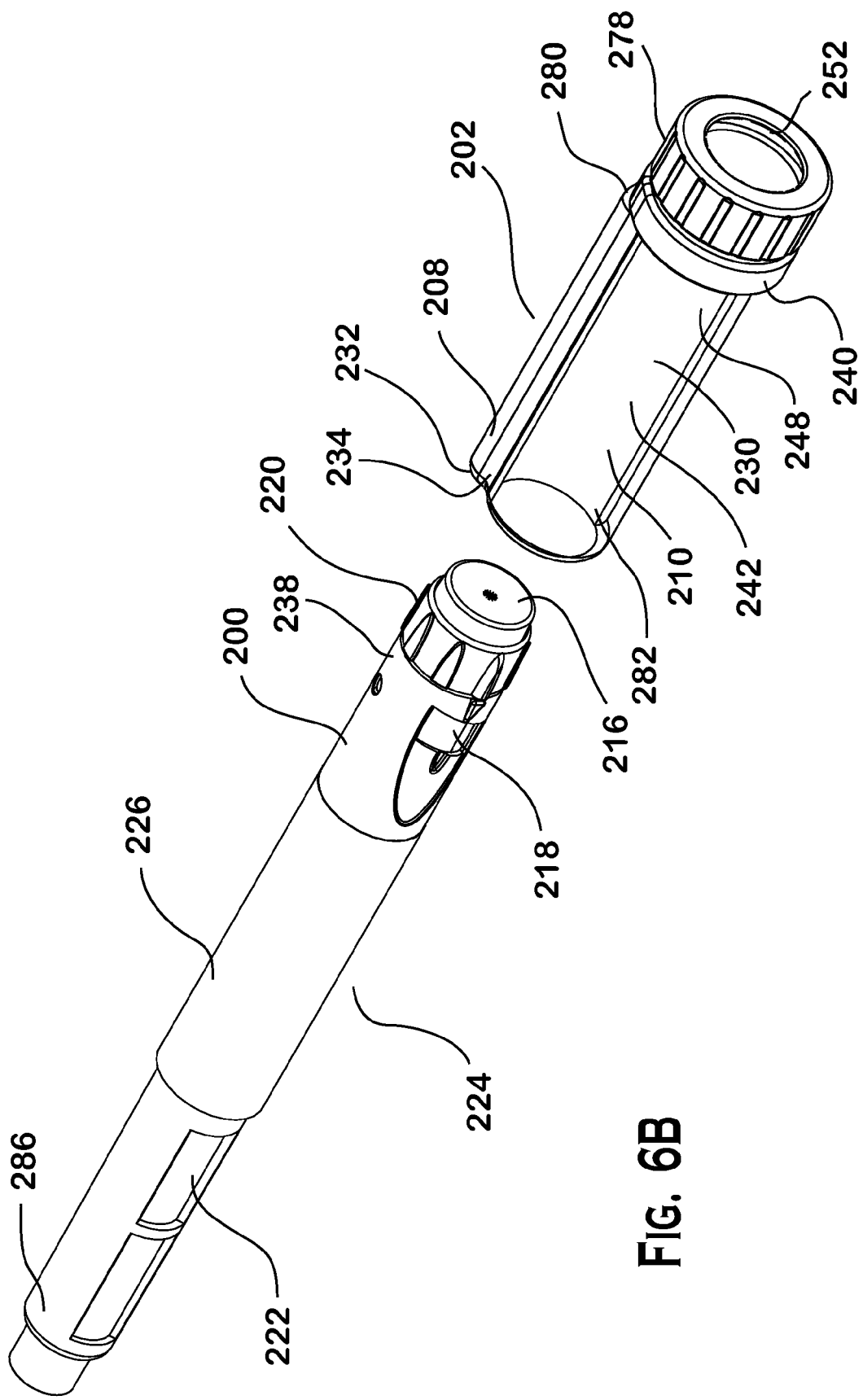
FIG. 6B illustrates a perspective view of a drug delivery unit and the medical module prior to being coupled together.
Figure 6C:
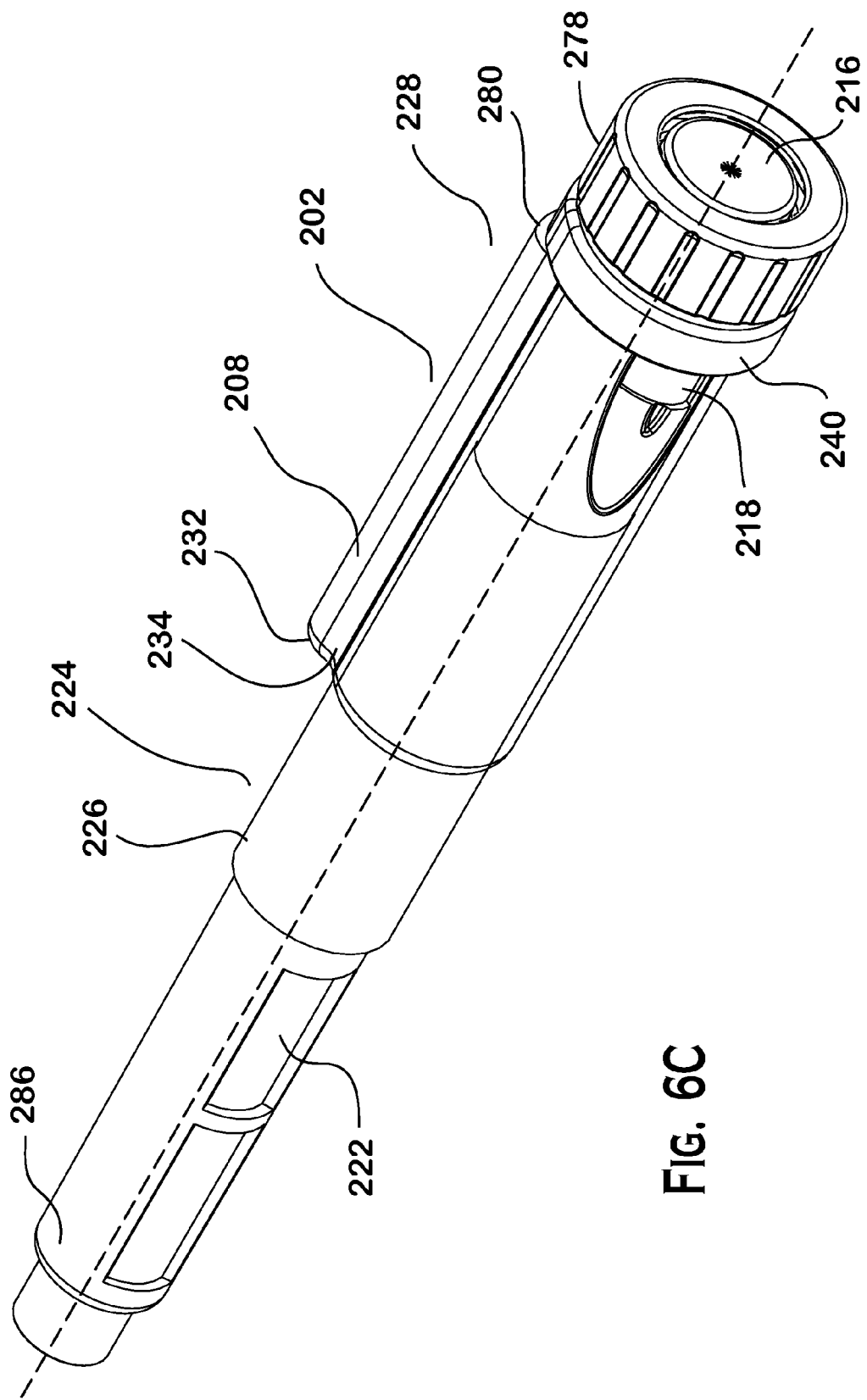
FIG. 6C illustrates a perspective view of a medical module and a drug delivery pen as coupled together.

Referring to FIGS. 6A and 6B, module 202 is provided with housing 209. Module 202 is provided with casing 208 that extends along longitudinal axis L1 so that the casing 208 covers the outer surface of housing 209. That is, casing 208 includes three wall surfaces that together with outer surface 210 of housing 209 provides for an enclosure of certain components. Casing 208 encloses circuit board 270 (see FIG. 6D), sensor 214 (which includes a sensor slider 215) and power supply 276 which are disposed on top of outer surface 210 of housing 209. Power supply 276 is accessible through power supply compartment door provided on casing 208. Because casing 208 is disposed over outer surface 210 of housing 209, casing 208 is located asymmetrically with respect to longitudinal axis L2 of housing 209. To further reduce the offset profile of casing 208, power supply 276 may be located proximate knob 278 instead of inside casing 208.

Referring back to FIG. 6A, housing 209 extends from a first end 232 to second end 280 along longitudinal axis L2 to define at least a portion of a hollow bore 248. Coupled to housing 209 is a 240, with knob 278 disposed about aperture 252. Both of follower portion 240 and knob 278 are preferably continuous through-bores that are in alignment with bore 248. Bore 248 is configured to allow actuation unit 200 of drug delivery pen 224 (see FIG. 6B) to be slipped into bore 248 until actuation button 216 of pen 224 protrudes through opening 252. In the preferred embodiment of FIG. 6A, bore 248 is a through-bore which is contiguous with the bore of rotatable knob 278 and continuous surface 210 of housing 209 defines a generally tubular member. The knob 278 is physically coupled to the follower portion 240, and the follower portion 240 is directly and physically connected to slider 215 of sensor 214 via longitudinal member 254 such that movement of the knob 278 results in corresponding proportional movements of follower 240 and slider 215. To allow for visual inspection of printed indicia on drug delivery pen 200 or to allow for reading of the dose display 218, a portion of housing 209 is preferably substantially transparent.

Applicants have recognized that, on certain conventional insulin pens, there are provided at least a raised ridge 210b, shown, for example, in FIG. 7D. Applicants have recognized that raised ridge 210b of such pens may be used to provide a positive coupling between unit 102 and the drug delivery pen. Specifically, unit 202 may be provided with a recessed groove on the inner surface of housing 209 that is in a mating arrangement with raised ridge 210b to align unit 202 and prevent the rotation of unit 202 with respect to pen 124.

Figure 6D:
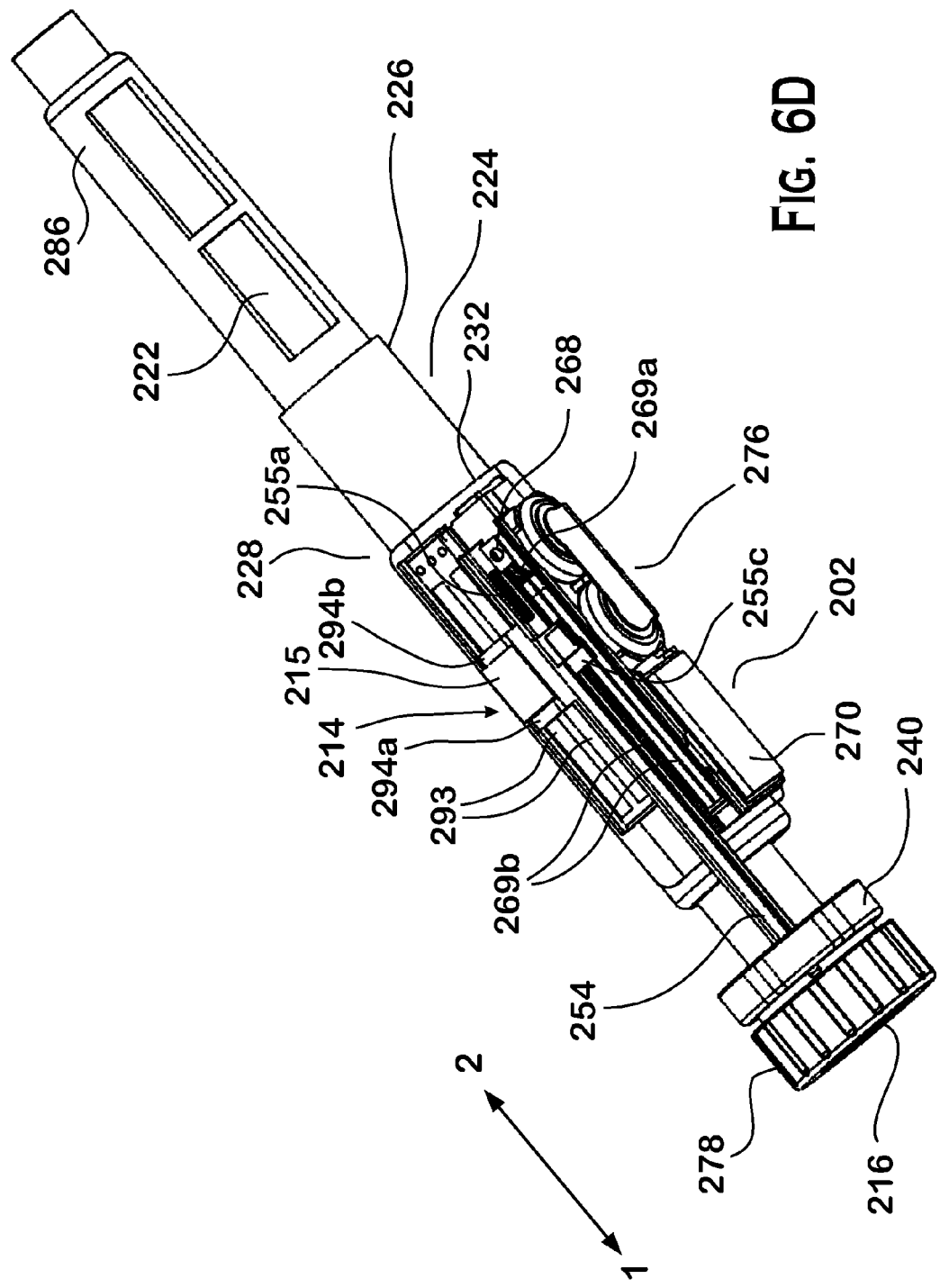
FIG. 6D illustrates the rear perspective view of FIG. 6C, where the rotatable knob, the dosage delivery button, the follower portion, and the longitudinal member have been extended, prior to dose delivery, according to an exemplary embodiment described and illustrated herein.
Figure 7E:
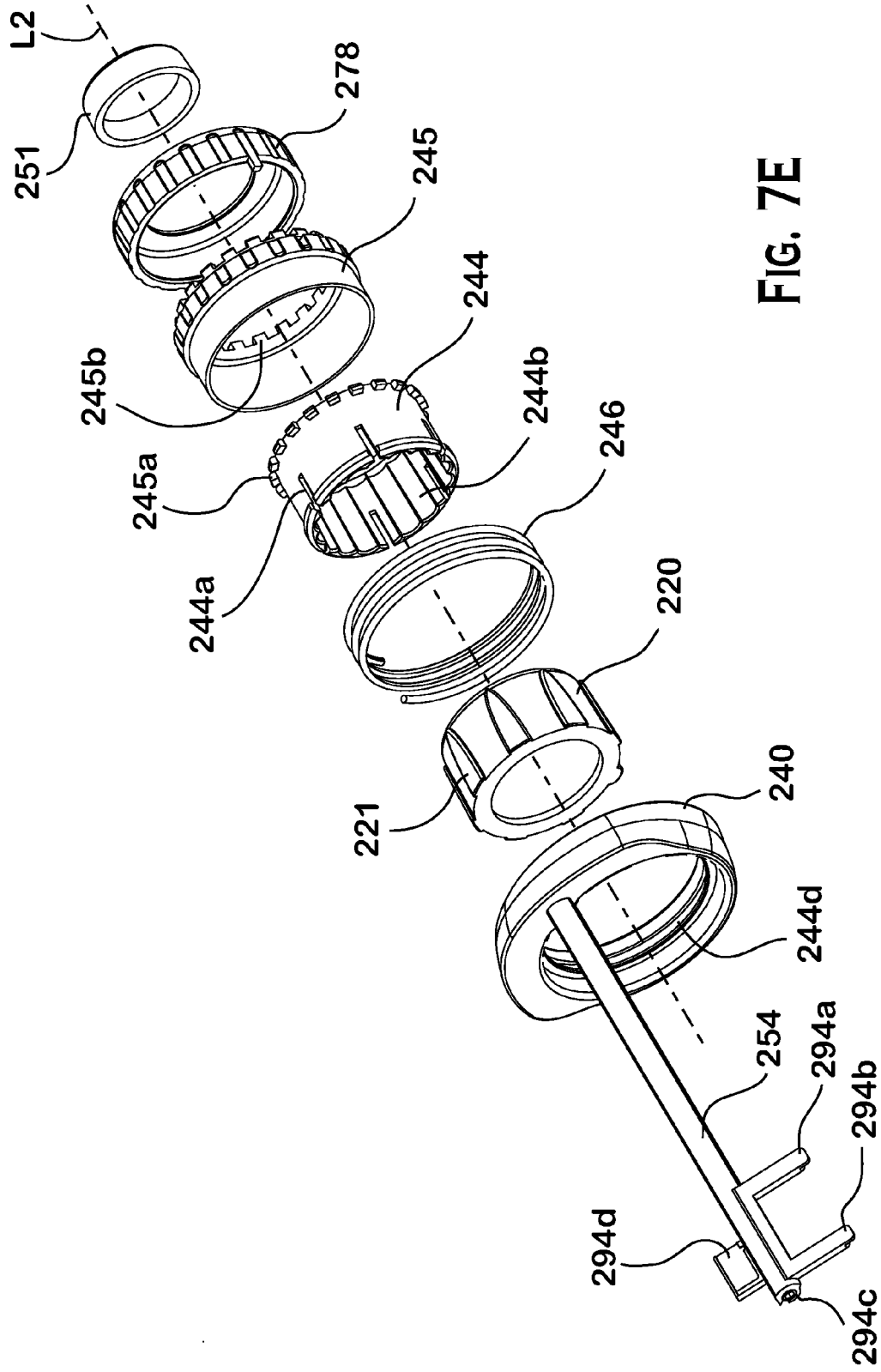
FIG. 7E illustrates an exploded view of components of the unit coupled to an actuation unit of the drug delivery device of FIG. 7B.

To reduce the profile of unit 202, applicants have utilized a sliding potentiometer configuration shown here in FIG. 6D. In this embodiment, a slider 215 is connected to longitudinal member 254, which is connected to follower portion 240. Longitudinal member 254 is provided with slider fingers 294a and 294b, which are used to retain a slider 215. Follower 240 may be coupled to a dosage selector 220 by a suitable coupling arrangement, such as, for example, via a slip fit coupling with ring-like member interposed between follower 240 and the dosage selector or an arrangement adapted from the arrangement shown in FIG. 7E. In the adaptation of FIG. 7E, follower 240 is coupled to a capture ring 244 via a groove retention mechanism that includes groove 244d on follower member 240 and corresponding ridge 244c on capture ring 244. Capture ring 244 may include longitudinal slits 244a that extend along longitudinal axis L2. Longitudinal slits 244a provide flexibility in the diameter of capture ring 244 which allow inner undulating surfaces 244b of capture ring 244 to frictionally couple to dosage selector 220 (of pen 224) via raised ribs 221. Undulating surfaces 244b may be configured to allow for a taper towards axis L2 to ensure little or no interference with ribs 221 when they first engage undulation 244b but with frictional engagement upon full insertion. Capture ring 244 may be provided with external splines or teeth 245a that are in engagement with internal splines or teeth 245b of rotatable knob 278. Rotatable knob 278 is provided with a through opening 252 to allow actuation button 216 of pen 202 to protrude through such opening 252 for engagement by the user.

It should be noted that rotatable knob 278 disengages from capture ring 244 during injection so that the knob does not rotate under the user's thumb while drug is being delivered, i.e., during the injection. After injecting, teeth 245a re-engage with teeth 245b, allowing the user to dial in a new dose on the pen. Knob 278, however, may need to be rotated slightly before the teeth re-engage if they are not properly lined up after the injection.

Referring to FIG. 6D, longitudinal member 254 may be configured to slide axially along axis L2 as knob 278 is moved axially by rotating knob 278 about axis L2. In this figure, slider 215 is shown positioned proximately mid-way on potentiometer tracks 293. As knob 278 is rotated to translate knob 278 along axis L2, capture ring 244 is constrained to also rotate, which causes the rotational motion of capture ring 244 to be transferred to dosage selector 220, which then causes dosage selector 220 to also rotate and translate. Since any rotary motion of selector 220 will results in axial movement along axis L2, capture ring 244, follower 240, and knob 278 are constrained to move in the same manner as dosage selector 220 (axially for follower 240, and both axially and rotationally for capture ring 244 and knob 278). Hence, movements of the dosage selector 220 are determined via the potentiometer as proportional to a dosage quantity to be delivered or injected. In the preferred embodiments, potentiometer tracks 293 may be conductive polymer tracks or cerement tracks. In the embodiment of FIG. 6B, the drug delivery pen may be a Lantus SoloStar insulin manufactured by Sanofi-Aventis.

In FIG. 6D, longitudinal member 254 is connected to a separator member 255c which interacts with fingers 269a of micro switch 268 to allow for a determination of a drug delivery event. Because fingers 269a are normally not in contact with conductive tracks 269b, switch 268 is normally opened whenever button 216 is not depressed fully (e.g., during a dosage selection or adjustment). Upon button 216 being fully depressed in direction 2, longitudinal member 254 and separator 255c are constrained to move along longitudinal axis L1 until spring 255a is fully compressed to abut against a stop surface (not shown) in casing 208. As spring 255a approaches the stop surface, separator 255c lowers fingers 269a of micro switch 268 onto conductive tracks 269b, creating a closed-circuit. Movement of the button 216 in direction 2 separates fingers 269a whereas movement in direction 1 causes the fingers 269a to contact conductive tracks 269b and forming a closed-circuit, i.e., in the manner of a momentary switch.

Third Type of Module

Referring to FIGS. 7A and 7B, an alternative module 204 is provided with several distinct features from the previously described module 202. Like module 202, this module 204 has a housing 209. Module 204 is also provided with casing 208 that extends along longitudinal axis L1 so that the casing 208 covers the outer surface of housing 209. That is, casing 208 includes three wall surfaces that together with the outer surface 210 of housing 209 provides for enclosure of certain components. Casing 208 encloses circuit board 270 (see FIG. 8A), sensor 214 (which includes a sensor slider 215) and power supply 276 which are disposed on top of outer surface 210 of housing 209. Power supply 276 is accessible through power supply compartment door provided on casing 208. Because casing 208 is disposed over outer surface 210 of housing 209, casing 208 is located asymmetrically with respect to longitudinal axis L2 of housing 209. To further reduce the offset or asymmetric profile of casing 208, power supply 276 may be located proximate knob 278 instead of inside casing 208. As with the first and second module types, a hollow bore of the module is adapted to be coupled to a drug delivery pen in one operative mode and to be separated from the pen in another operative mode. Upon separation from the pen, the module is no longer coupled to the actuation mechanism of the pen and in fact is lacking in an actuation mechanism, e.g., a plunger, push rod, or the like, such that an internal surface of the hollow bore is exposed to the ambient environment so as to be visible to an ordinary observer or user. Housing 209 extends from a first end 232 to second end 280 along longitudinal axis L2 to define at least a portion of a hollow bore 248 formed from continuous surface 210 of housing 209. Continuous surface 210 is provided with a scallop portion 211 (FIGS. 7A and 7C) that is distinct from other embodiments. While a housing 209 can be formed from a substantially transparent or translucent material, such material can cause visual distortion of printed indicia on drug delivery pen 224. As such, scalloped opening 211 allows for printed identification on drug delivery device 224 to be visible to the user once unit 204 has been coupled to pen 224. Module 204 is coupled to drug delivery pen 224 by inserting bore 248 with scallop 211 closest to dosage selector 220 of pen 224 (FIGS. 1 and 1B). As module 204 is inserted onto pen 224, a groove 210a on module 204 (FIGS. 1 and 1B) is aligned with a raised ridge 210b on pen 224 to fix module 204 rotationally with respect to pen 224. In addition, a tang 236 may be used to engage to a recess in pen 224.

Coupled to housing 209 are a follower portion 240, and rotatable knob 278. Both of follower portion 240 and knob 278 are preferably continuous through-bores that are in alignment with bore 248. Bore 248 is configured to allow actuation unit 200 of drug delivery pen 224 (see FIG. 10) to be slipped into bore 248 until actuation button 216 of pen 224 abuts with button 251 of module 204. In the preferred embodiment of FIG. 7A, bore 248 is a through bore which is contiguous with bore of rotatable knob 278 and continuous surface 210 of housing 209 defines a generally tubular member. As noted earlier, secondary-housing 209 is preferably formed from a substantially transparent or translucent material while casing 208 may be formed with any suitable color or combination of colors. As used herein, the actuation unit 200 of a drug delivery pen is that portion of the pen on which at least the dosage selector, actuator and actuation button are provided for attachment to a drug cartridge 222.

Module 204 is coupled to drug delivery pen 224 by inserting bore 248 with scallop 211 closest to dosage selector 220 of pen 224 (FIG. 7D). As module 204 is inserted onto pen 224, a groove 210a on module 204 (FIG. 7A) is aligned with a raised ridge 210b on pen 224 to fix module 204 rotationally with respect to pen 224.

Figure 8A:
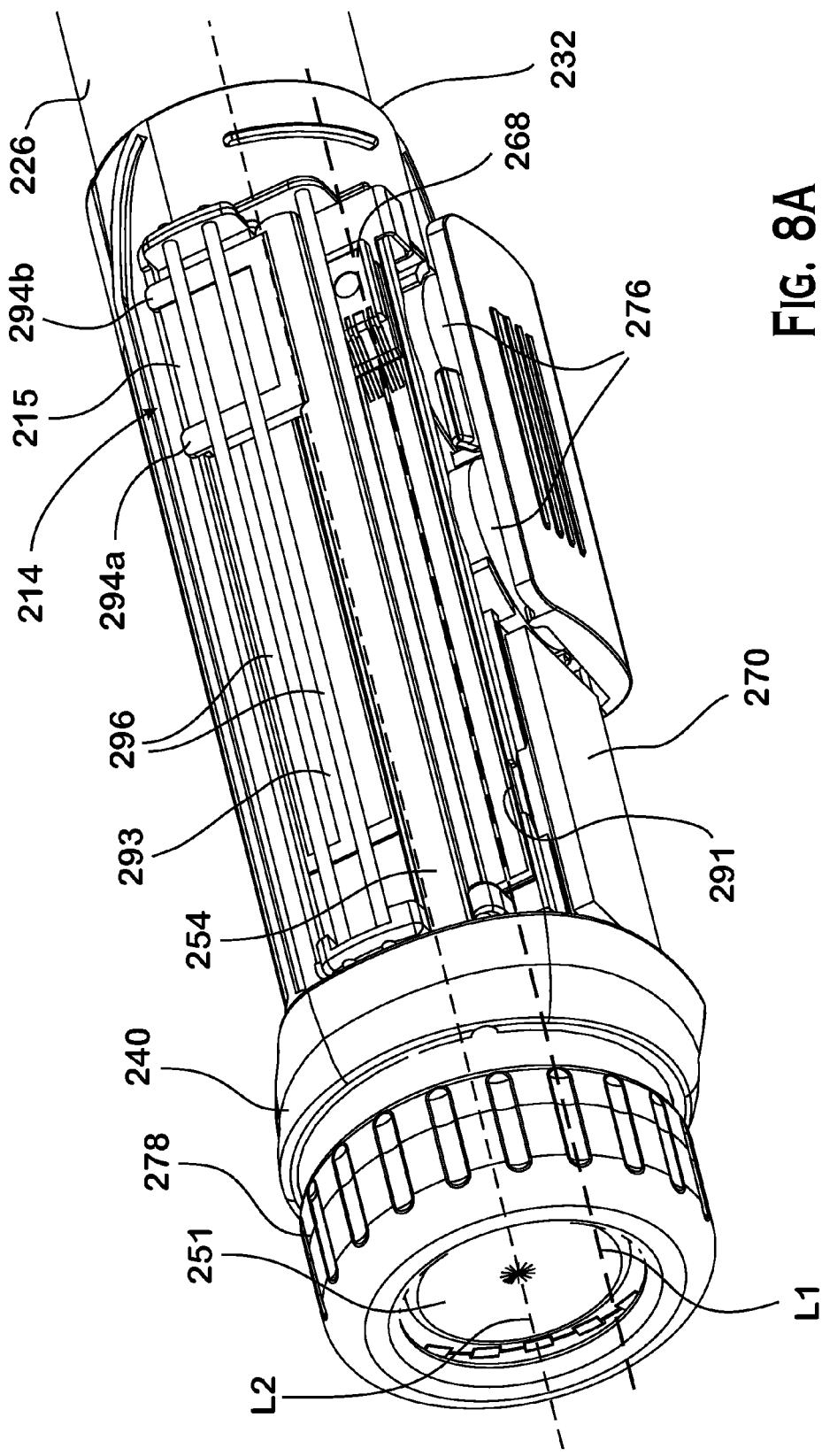
FIG. 8A illustrates a rear perspective view with a cover removed to show internal components of the unit of FIG. 7A.

Referring to FIG. 8A, module 204 also utilizes a slider 215 on potentiometer tracks, which slider 215 is connected to longitudinal member 254, which is connected to follower portion 240. Longitudinal member 254 is provided with slider fingers 294a and 294b, which are used to retain a slider 215 (FIG. 8A) along with retention rods 296 (FIG. 8B) to ensure that the slider is constrained for translation along axis L1.

As shown in FIG. 7E, follower 240 is coupled to capture ring 244 via a retention system having groove 244d on follower member 240 and corresponding ridge 244c on capture ring 244. Follower 240 and capture ring 244 can be coupled together such that capture ring 244 is rotatable around second longitudinal axis L2 and that follower 240 does not rotate, but moves in a linear manner parallel to second longitudinal axis L2.

Capture ring 244 may include longitudinal slits 244a that extend along longitudinal axis L2 to provide flexibility in the magnitude of the diameter of capture ring 244, which allows inner undulating surfaces 244b of capture ring 244 to frictionally couple to raised ribs 221 of dosage selector 220 (of pen 224). Inner undulating surfaces 244b may be configured to allow for a taper converging towards axis L2 to ensure little or no interference when ribs 221 first engage undulation 244b yet with frictional engagement upon full insertion of module 204 into pen 224. Capture ring 244 may be provided with external splines or teeth 245a that are in engagement with internal splines or teeth 245b of a coupling ring 245. Coupling ring 245 can couple together rotatable knob 278 and capture ring 244. The mechanical assembly of capture ring 244, coupling ring 245, and rotatable knob 278 causes dosage selector 220 to rotate as a result of a rotation of rotating knob 278 when the dosage selector 220 is frictionally engaged.

Actuation button 251 is also coupled to knob 278 so that button 251 of module 202 is in contact with pen button 216 once both components are assembled together. A spring 246 can be located on an outer surface of capture ring 244 and an inner surface of knob 278. Spring 246 can be configured to bias coupling ring 245 against capture ring 244 such that when teeth 245a are engaged, turning knob 278 causes dosage selector 220 to turn. During an injection, pressing button 251 can compress spring 246, allowing coupling ring 245 to disengage from capture ring 244. It should be noted that rotatable knob 278 disengages from capture ring 244 during actual injection so that the knob does not rotate under the user's thumb while drug is being delivered, i.e., dosage on the pen. Follower 240 can include a longitudinal member 254, as illustrated in FIG. 7E. Longitudinal member can have a tubular structure where one end is coupled to a ring portion of the follower 240. A hollow portion 294c of the tubular structure is depicted in FIG. 7E. The other end of longitudinal member can have a protrusion plate 294d and two slider fingers 294a and 294b.

Referring to FIG. 8A, longitudinal member 254 may be configured to slide axially along axis L2. Follower portion 240 is constrained to move with knob 278 as knob 278 is moved axially by rotating knob 278 about axis L2. As knob 278 is rotated, capture ring 244 is constrained to also rotate, which causes the rotational motion of capture ring 244 to be transferred to dosage selector 220. Since any rotary motion of selector 220 will result in inward or outward axial movement along axis L2, capture ring 244, follower 240, and knob 278 are constrained to move in the same manner as dosage selector 220 (axially for follower 240, and both axially and rotationally for capture ring 244 and knob 278). Hence, movements of the dosage selector 220 are determined via a dosage sensor 214 as proportional to a dosage quantity to be delivered or injected. In the preferred embodiments, the dosage sensor, which provides dosage amount information, is a potentiometer. In the embodiment of FIG. 7B, the drug delivery pen may be a Lantus SoloStar manufactured by Sanofi Aventis.

Figure 8B:
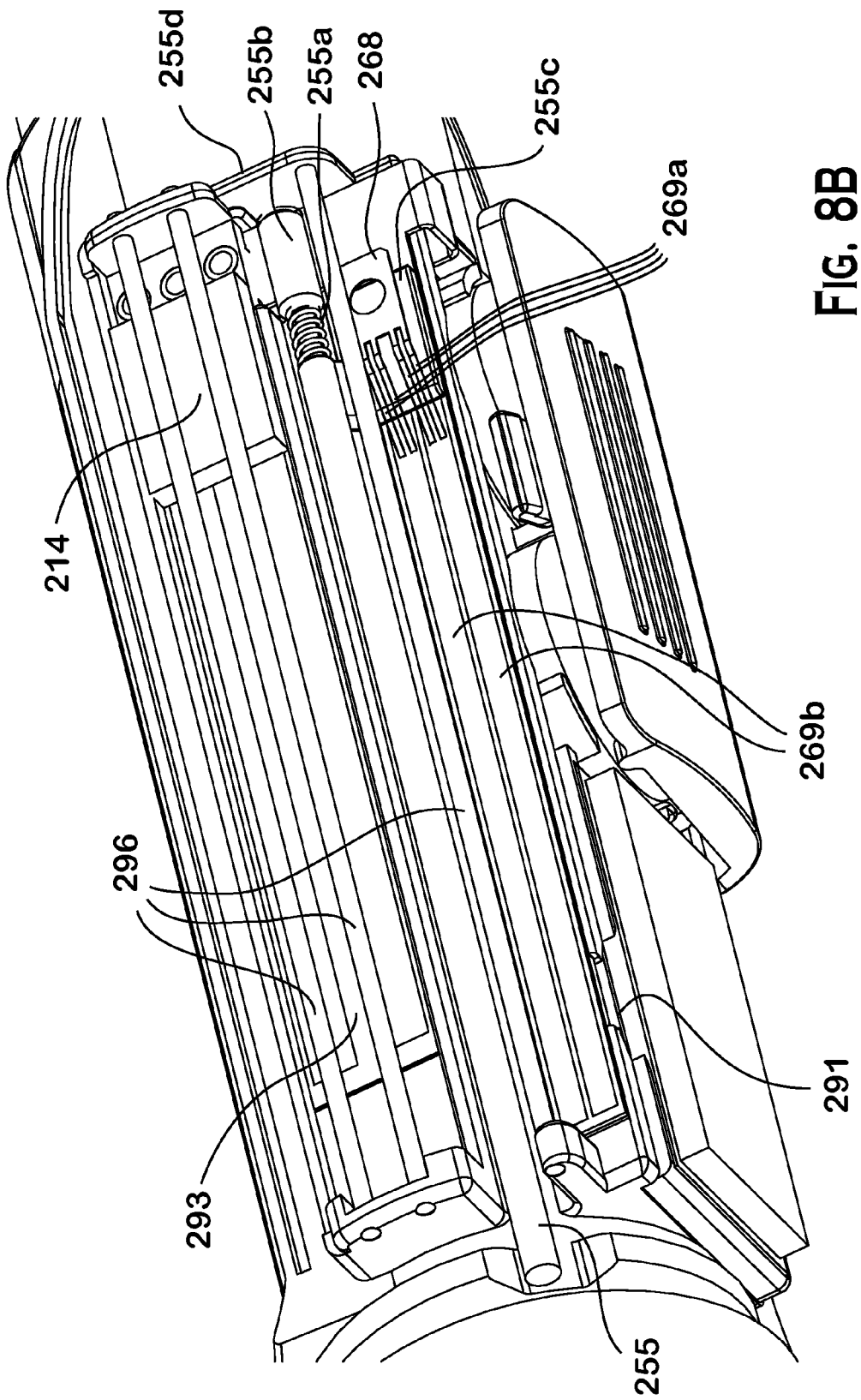
FIG. 8B illustrates a close-up rear perspective view of FIG. 8A to show the components utilized in determining dosage selection, delivery and duration of delivery.

Referring to FIG. 8B, longitudinal member 254 is removed to show activation shaft 297 that was disposed inside longitudinal member 254. Activation shaft 297 is connected to a separator member 255c, which interacts with fingers 269a of micro switch 268. Hollow portion 294c and protrusion plate 294d can be keyed to correspond to separator member 255c so that separator member moves along axis L1 when button 251 is depressed. Activation shaft 297 may be coupled with a spring 255a and a setscrew 255b for adjustment of the position of separator 255c with respect to fingers 269a of micro switch 268. Because fingers 269a are normally out of contact with conductive tracks 269b, switch 268 is normally-open whenever button 251 is not depressed fully (e.g., during a dosage selection or adjustment). Upon button 251 being fully depressed, such as during a dosage injection, longitudinal member 254, activation shaft 297, and separator 255c are constrained to move along longitudinal axis L1 until setscrew 255b abuts against retainer wall 255d. As setscrew 255b approaches retainer wall 255d, separator 255c lowers fingers 269a of micro switch 268 onto conductive tracks 269b, creating a closed circuit. Further movement of dosage button 251 causes hollow longitudinal member 254 to continue axially to take up any slack provided between an end of a rod portion of activation shaft and setscrew 255b.

By virtue of the configurations described exemplarily herein, applicants have now been able to provide the means for determining the difference between either or both of a dosage delivery event and duration of such dosage delivery or injection event. Specifically, where a user is merely rotating knob 278 to thereby move knob 278 longitudinally along axis L2 in either direction to select dosages, there is no contact of fingers 269a of switch 268 and hence no determination that a dosage event is taking place. Except for a determination that a dosage selection is being made, no recording is made in the memory of processor board 270 regarding a dosage delivery. Only upon the full depression of button 251 would there be contact of fingers 269a with tracks 269b, (FIGS. 8A and 8B) triggering a determination that dosage delivery is taking place. In an embodiment, the electronics can be configured to go into "sleep" mode, until button 251 is depressed, which reduces the power consumption of the module. As used herein, the "sleep" mode is one in which all functionalities of the module are at minimal or virtually zero power consumption but which does not require a system boot up in the event that the pen is taken out of sleep mode.

It should be noted that the micro-switch 268 also enables tracking of the injection start point and the injection end point, so the volume of the injection can be calculated, even if the user does not press the injector button all the way to the zero dosage position. While the ability to determine when a dosage delivery has been made is valuable to a user in managing diabetes, applicants believe that it is the ability to determine and confirm the duration of such dosage delivery for later analysis with a compliance regiment that is a step forward in the art of diabetes management. That is, where a patient is injecting insulin per a protocol as prescribed by a health care provider, such patient may not be in full compliance if the patient fails to deliver a complete prescribed dosage, which typically requires fully depressing button 251 for four (4) to ten (10) seconds. By recording the dosage, time and duration in memory of processor board 270 for transfer to a health care provider's computer, the health care provider is able to take steps, after review of data or even in real-time, to ensure that full compliance of the prescribed protocol is followed. In the preferred embodiments, a warning or reminder to the patient on proper pen usage technique can be displayed as a message on the data management unit, which in one embodiment includes a glucose meter. Thus, the means for determining one or more of dosage delivery or duration of dosage delivery of a drug delivery pen include, follower 240, longitudinal member 254, spring 255a, separator 269a, switch 268, a processor coupled to switch 268, in which processor is programmed to operate in the manner described herein, and equivalents to these components.

Fourth Type of Module

Recognizing that different drug delivery devices (e.g., insulin pens) may be required based on user preferences, applicants have provided for an alternative type of module 402, as illustrated in FIG. 9A, which is usable with a drug delivery pen, as illustrated in FIG. 9B. In this embodiment, applicants have provided for an alternative that is designed to further reduce the offset or asymmetric profile. Additionally, applicants have provided for an alternative that has a mechanism for easily changing the batteries. Add-on module 402 can include a primary module housing 408, a secondary module housing 409, a rotatable knob 478, a button 451, and a slot 451a. A power supply can be in the form of a disk shape (e.g., coin cell battery) similar in shape to a button 451. The battery can be disposed proximate to button 451 in a stacking relationship. Slot 451a can be used to rotate button 451 using a coin or screwdriver to easily remove button 451 so that the battery can be changed.

Other Variations of the Add-On Module

Figure 10A:
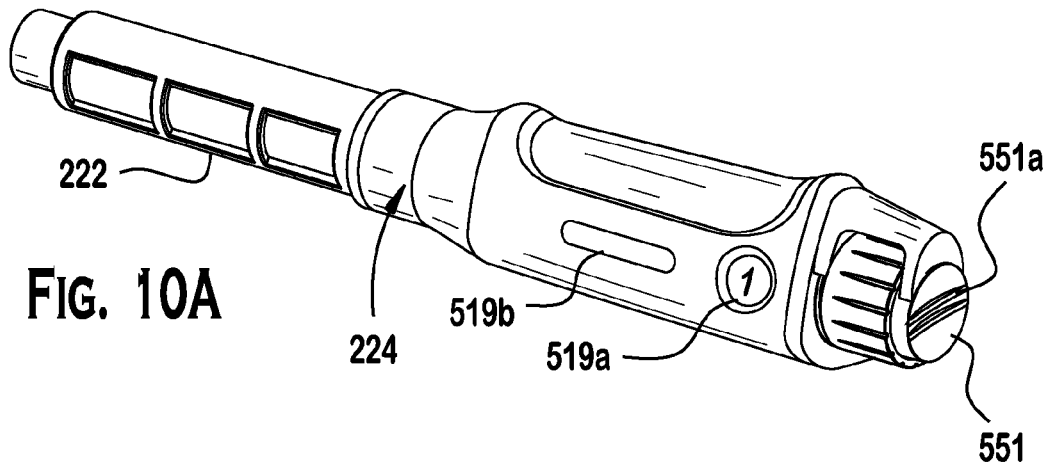
FIGS. 10A, 10B, and 10C illustrate respective variations of the modules described earlier.

FIG. 10A illustrates another embodiment of a module 502 that is similar to module 102. Add-on module 502 does not have a first and second extension portions like module 102. Instead, module 502 has a housing that wraps around the drug delivery pen. The housing of module 502 has two windows 519a and 519b for allowing the user to view display window and written indicia on the pen. Add-on module 502 includes a button 551 and a slot 551a. A power supply can be in the form of a disk shape (e.g., coin cell battery) similar in shape to a button 551. The battery can be disposed proximate to button 551 in a stacking relationship. Slot 551a can be used to rotate button 451 using a coin or screw driver to easily remove button 551 so that the battery can be changed.

Figure 10B:
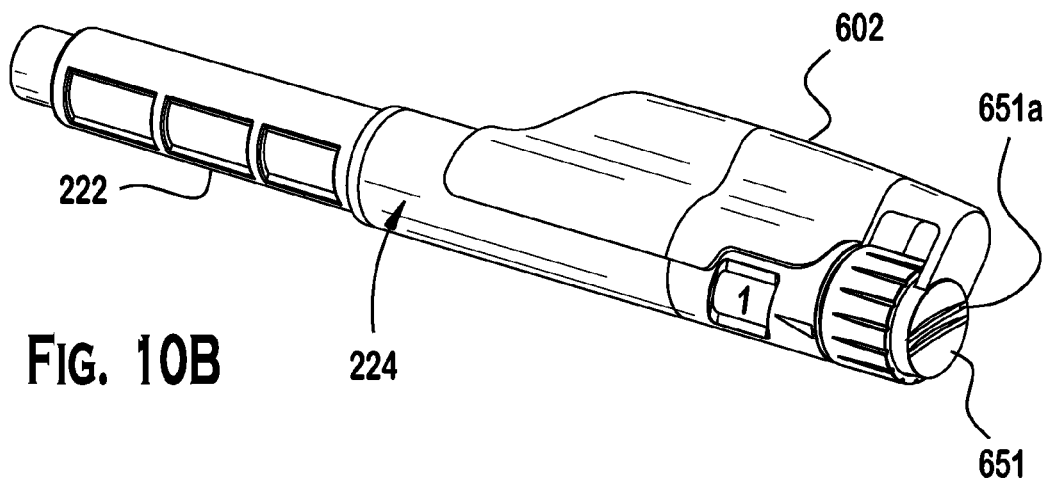

FIG. 10B illustrates another embodiment of a module 602 that is similar to module 102. Add-on module 602 includes a button 651 and a slot 651a that are similar to module 502.

Figure 10C:
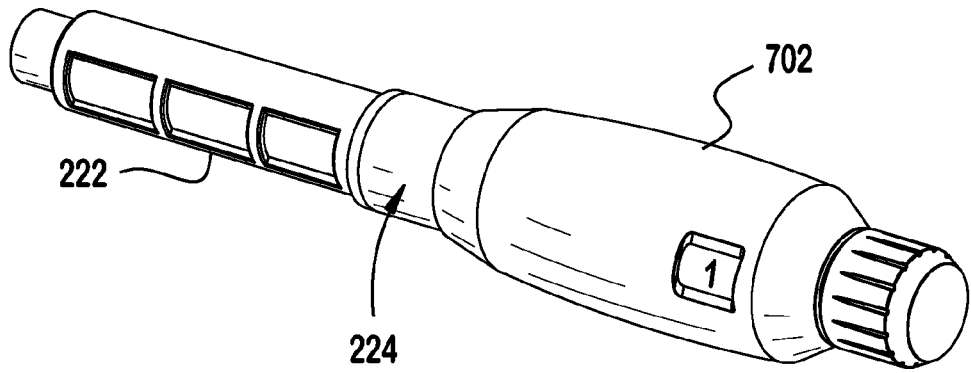

FIG. 10C illustrates another embodiment of a module 702 that is similar to module 204. In contrast to previous embodiments, module 702 has a housing that is symmetrical with respect to a longitudinal axis that extends along the pen. The housing of module 702 has a window 719 for allowing the user to view display window on the pen.

Operation of the Exemplary Embodiments

In use, a user would couple (e.g., snap-on, slide on, close a clam-shell) the medical module (102, 202, 204, 402, 502, 602, or 702) over actuation end 100 (or 200) of a drug delivery pen 124 (or 224), as shown herein the figures. Once the medical module (102, 202, 204, 402, 502, 602, or 702) has been coupled to drug delivery pen 124 (or 224), turning dosage selector 120 (or rotating knob 278) allows the user to dial in a dosage for injection. The selected dosage appears in dosage indicator window 118 (or 218) of the pen 124 or 224. As dosage selector 120 rotates, it extends shaft 190 within drug delivery pen 124 (or 224), illustrated in FIGS. 5 and 6D, causing longitudinal member 154 (or 254) to extend as well. Similarly, as knob 278 rotates, it extends longitudinal member 254 within the primary module housing 208, as illustrated in FIG. 8A. The amount of insulin to be injected is proportional to the extension of shaft 190 (FIG. 5) of pen 124 and longitudinal member 154, which is measured by dosage sensor 114. Similarly, the amount of insulin to be injected is proportional to the extension of follower 240 of module 202 and longitudinal member 254, which is measured by dosage sensor 214. Dosage selector 120 (or knob 278) may be rotated in either direction, increasing or decreasing the selected dosage.

A suitable needle (not shown) can be attached to the insulin cartridge 122 or 222. Before injecting, the user primes drug delivery pen 124 or 224 by ejecting a small dose (typically 2 Units) before inserting a needle subcutaneously. Priming drug delivery pen 124 or 224 eliminates bubbles. While priming, drug delivery pen 124 or 224 should be held with needle pointing upwards. Medical module 102 may distinguish between primes and injections by two exemplary techniques: (1) it may determine via an inertial or acceleration sensor disposed in the housing of the add-on module if drug delivery pen 124 or 224 is held with needle pointing upward (in relation to the ground) during an injection, and (2) it may use software to determine if one or more small doses of approximately 2 Units are followed by a larger dose. In some cases, a separate glucose meter may ask the user to confirm whether a dose was a prime or an injection. In an embodiment, the inertial sensor can also be used to wake up the device if it is in sleep mode when the device is picked up by the user. In the dosing history menu on the glucose meter (not shown), it is possible for the user to toggle entries between prime and injection. As an example, the meter can display primes by indicating with the symbol "*" (for example) which injections were preceded by a prime. Applicant believes that this allows the displaying of as much information as possible on one screen on the meter without confusing the user by showing all the primes and injection doses together in one list.

After dialing in the desired dose, the injection is performed by inserting the needle into the skin and with the user's thumb fully depressing actuation button 116 of pen 124 (for module 102), button 216 of pen 224, or button 251 (for module 202). Once the actuation button is fully depressed, the button must be held down for a predetermined period of time for the selected dosage to be fully injected. As provided in the means for determining dosage injection event and duration thereof, the add-on module records such an event and the duration of the event into its memory. The user may perform this sequence until the cartridge 222 is depleted.

After insulin cartridge 222 is depleted, module 102 (202 or 204) is removed from disposable drug delivery pen 124 (or 224), disposable drug delivery pen 124 or 224 (e.g., an insulin pen) is thrown away, and module 102 is re-attached to a new disposable drug delivery device 124 or 224 (e.g., an insulin pen). Alternatively, where the user is using a reusable pen, the empty drug cartridge could be thrown away and replaced with a new cartridge attached to the actuation portion of the reusable pen.

As noted earlier, the single glucose meter may communicate with multiple medical modules. For example, glucose meter may communicate with a medical module (102, 202, 204, 402, 502, 602, or 702) attached to a rapid acting insulin drug delivery pen and another unit (102, 202, 204, 402, 502, 602, or 702) with a long acting insulin drug delivery pen. Medical modules (102, 202, 204, 402, 502, 602, or 702) may be color coded to match the color of drug delivery pens 124 or 224, identifying the type of insulin that it contains. This feature will help prevent accidental injections of the wrong type of insulin. In an embodiment, the module can be configured to attach to a specific type of pen housing in order to identify the type of insulin. In this embodiment the insulin pen manufacturer provides different type of pen housing shapes for specific types of insulin.

While some features have been described, other variations on the exemplary embodiments may be utilized in various combinations. For example, instead of a potentiometer, the add-on modules may use an encoder to measure angular position and rotation of dosage selector. A switch may be used with the encoder to detect when the user presses on dosage actuation button of the add-on module (102, 202, 204, 402, 502, 602, or 702) to inject a drug, such as, for example, insulin, and allows for differentiation between dosage adjustments and injections. Such switch also detects how long the user continues to press on the dosage actuation button after injecting an insulin shot, as described earlier. In another example, when the switch is activated and after the encoder determines that dosage selector dial has returned to the zero position, the add-on module (102, 202, 204, 402, 502, 602, or 702) may communicate this information to the blood glucose meter to initiate a timer on the meter that counts down the period of time that the user should keep the dial depressed. If the user releases pressure on the switch prematurely, a warning may be announced or displayed on the blood glucose meter. Alternatively or in addition, a small display or LEDs on the snap-on pen module (102, 202, 204, 402, 502, 602, or 702) may be used to cue the user as to how long to press on the dial. It is noted, however, that a display is not absolutely necessary—the device could just track the time that the button is depressed and display a message/warning on the meter if the user does not hold down the button for a sufficient amount of time. The switch may also be configured to work with sensors other than encoders, for example the linear potentiometer as shown exemplarily in FIGS. 1-8. Medical module (102, 202, 204, 402, 502, 602, or 702) 102 may include various features that guide users in the proper use of drug delivery pens 124 or 224. For example, medical module (102, 202, 204, 402, 502, 602, or 702) can: alert the user if they have not primed drug delivery pen 124 or 224 using the inertial sensor; alert the user if a mixing step has not been performed (applicable to mixed insulins) using the inertial sensor; warn the user if the injection is incomplete (i.e., dosage delivery button is not pressed all the way to zero); provide a timer that reminds the user to hold dosage delivery button 116 down for several seconds during an injection; keep track of remaining insulin in drug delivery pen 124 or 224; remind user when it is time to inject; alert the user if injections have been missed or duplicated; alert the user if insulin is about to expire.

In addition, medical module (102, 202, 204, 402, 502, 602, or 702) may include a micro switch in module housing 108 to allow for activation of certain features. For example, the insertion of drug delivery pen 124 or 224 into medical module (102, 202, 204, 402, 502, 602, or 702) triggers the micro switch. Triggering the micro switch serves two purposes: first, it signals when a new drug delivery pen 124 or 224 is inserted, which allows medical module (102, 202, 204, 402, 502, 602, or 702) to track how much insulin is left in drug delivery pen 124 or 224; and second, it ensures that drug delivery pen 124 or 224 is inserted correctly, and is properly aligned with medical module.

Another feature that may be included in module is a technique for distinguishing a priming dose from a dose that is injected into the user. For example, a gravity or inertial sensor may be used to determine if the device is pointing upwards when dial 3 is pressed, indicating a priming shot since the device is held in an inverted position when purging bubbles. The add-on module is able to distinguish priming shots from actual drug delivery. For example, priming shots are typically two units or less, making them distinguishable from larger injected shots, and a priming shot will typically be followed by an injected shot, a pattern that may be distinguished in software. Similarly, it is useful to be able to distinguish between dosage size adjustments in which the user turns the dial backwards and/or forwards to dial in a specific dosage vs. movement of the dial position from the user injecting a shot. This is detectable by the microcontroller via the dosage sensor as well, since injections into the user should end with the dial returned to the initial, or home position, whereas adjustments of the dial to modify the dosage typically occur when the dial is set at a larger dosage and do not terminate in the initial, or home position of the dial.

Several features may be utilized to reduce inaccuracies in the use of insulin pens. These include missing injections, duplicating injections, and improper priming. Improper priming is especially problematic if a needle (not shown) was left on between doses, allowing air to enter drug cartridge 122. Some insulins, such as 70/30 pre-mix, must be mixed prior to injection. Neglecting to mix or improperly mixing 70/30 pre-mix before injection is a source of inaccuracy. Dosage delivery button 116 should be held for approximately 6 seconds during an injection to ensure the entire dose enters the body. Not holding dosage delivery button 116 long enough results in a partial dose. Medical module alerts the user to these inaccuracies and thus helps to reduce them.

As mentioned previously, the medical module (102, 202, 204, 402, 502, 602, or 702) may be used to measure insulin doses and transfer that information to a data management unit, which may be a glucose meter or a suitable data communication unit such as a mobile phone, home computer, mobile computer, server, monitoring network or even an insulin pump or combined insulin pump and controller or the like. The information that is transferred from medical module to the data management unit may be used to help master the use of drug delivery pen 124 or 224. Large potential sources of inaccuracy in the use of drug delivery pen 124 or 224 are missed doses and double doses. Medical module, as embodied herein, may help eliminate these sources of error by reminding the user of their dosing history. The complete dosing history (including doses and time and date the doses were delivered) may be made available to the user by selecting this option from the data management unit's menu. In addition, by having the most recent dosing information (time and amount) on a meter's display when the data management unit turns on, the user will immediately see if they have forgotten an injection every time they take a blood glucose measurement. In the same way that a data management unit may be used to alert a user when it's time to test blood glucose, the data management unit may also alert the user when to take insulin, or if an insulin injection has been missed. This information may also be displayed when the data management unit turns on.

Another source of inaccuracy when using drug delivery pens 124 or 224 is improper priming technique (or failing to prime altogether). The purpose of priming (sometimes called a test injection) is to remove air bubbles from drug cartridge 122 and needle, which would reduce the volume of an injection. Drug delivery pen 124 or 224 should be held vertically during priming so bubbles rise to the top of drug cartridge 122 (the end closest needle) and may be expelled by a priming dose. The priming is successful if the user sees a drop of insulin appear at the needle tip. If the user does not see a drop of insulin, the priming step is repeated. An inertial sensor is disposed in the module housing or located on the processor board 170 or 270 to detect if drug delivery pen 124 or 224 is held vertically during priming, and this information may be sent wirelessly to the data management unit. Low cost microelectromechanical systems (MEMS) inertial sensor chips are widely available, accurate, low cost, and small in size. Preferred inertial sensor may include Analog Devices model ADXL322 accelerometer (available at http://www.analog-.com/en/mems-and-sensors/imems-accelerometers/ADXL322/products/product.html#pricing). The data management unit may remind the user to hold drug delivery pen 124 or 224 vertically when priming, if they are not doing so. In addition, if the user skips the priming step altogether, this will be apparent from the information collected by medical module 102, 202, or 204, and a visual or auditory warning, reminder, and/or instructions may be given to the user by the add-on module or the data management unit.

The inertial sensor is also utilized to determine if the user is performing the proper mixing technique before injecting insulin, another source of error in using drug delivery pen 124 or 224. Some insulins must be mixed prior to use, such as 70/30 pre-mixed insulin. Mixing typically involves moving drug delivery pen 124 or 224 from straight up to straight down ten times, an action that is easily detectable by an inertial sensor (located in an attached medical module 102, 202, or 204. A message may be displayed on the data management unit to remind the patient how to mix their insulin if they are using insulin that requires mixing prior to use.

Another source of error related to priming is that of neglecting to remove and dispose of needles after each injection. The meter, in one embodiment, would provide a display to generate a reminder stating that the needle should be removed with every use. Alternatively, the speaker mounted in the add-on module can be utilized to prompt the user with tones or prestored phrases configured for specific geographical areas (e.g., German for modules distributed in Germany, French for modules distributed in France and so on). Additionally, the speaker in the add-on module may be configured to allow a user to locate a misplaced pen and module. Specifically, the add-on module may respond to an inquiry signal from a data management unit (or any electronic devices paired to the add-on module) to cause the speaker in the add-on module to emit tones or beeps in the event that the user has misplaced the pen and module. This method also can be used to confirm that a particular module is paired with a particular data management unit such as a glucose meter.

When injecting insulin with drug delivery pen 124 or 224, it is important to hold down on dosage delivery button 116 with needle inserted for approximately six seconds, to ensure that the entire dose is delivered below the skin. The optimal amount of time is usually spelled out in drug delivery pen 124 or 224 user's manual. A message may be displayed on either or both of the add-on module or the data management unit, reminding the user of proper technique if they are releasing dosage delivery button 116, 216 or 251 prematurely. The data management unit or the add-on module may display a countdown timer or emit a countdown tone or signals, initiated when dosage delivery button 116 is first pressed, letting the user know when they should release dosage delivery button 116.

Other pen-related usage reminders, such as the amount of time a pen may be used after removed from refrigeration, also may be incorporated into the smart pen module and displayed on the blood glucose meter as an aide to the user. To track the time a particular pen has been in use, the user would need to indicate the initiation of a new pen on the meter. In such embodiment, a switch is provided in the hollow bore of the smart pen module that is activated when it is attached to a pen, signaling the initiation of a new pen. The user may be asked to confirm on the meter when a new pen is initiated by pressing a button and possibly entering some information, such as the amount of insulin in the new pen.

In the examples given above, the add-on module (102, 202, 204, 402, 502, 602, or 702) is provided with a transceiver to allow receipt and transmission of information collected by the smart pen module to a cell phone or computer for easy look up or prominent display.

These features described and illustrated may be incorporated into a re-usable pen, in addition to a conventional disposable pen.

To our knowledge, no other device has sought to address the problems recognized here by applicants, with the exception of conventional digital insulin pens that display the last few injection amounts.

Several prototypes have been built that measure the amount of each dose and transmit this information to a meter for display. During evaluation of the prototypes, it was recognized by applicants that it would be useful to have the device communicate with multiple pens, since users often use one pen for long acting insulin and a separate pen for rapid acting insulin. In addition, some patients use more than one pen of the same type of insulin, placing them in different convenient locations (for example, at home, at work, in the car, etc.). Hence, applicants have realized that multiple modules may communicate with the data management unit (e.g., analyte meter, infusion pump or controller) for each of these pens to ensure that all insulin injections are captured. Also, it was further realized by applicants that the modules may be color-coded so that they would match the color of the drug delivery pen they are designed to work with. This feature is believed to be useful to users because insulin companies use the same pen to deliver different insulins, and they use color-coding to help the users distinguish between different pens. The modules may alert the user via a message, visual warning, or alarm on the add-on module(s) or meter as to the type of insulin they are injecting, helping them catch a potential error in which they might be injecting the wrong insulin—an error that may cause hypoglycemia or hyperglycemia.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A medical module comprising:
 a primary module housing extending along a first longitudinal axis from a first module housing end to a second module end;
 a secondary module housing coupled to the primary module, the secondary module extending along a second axis to define at least a portion of a hollow bore, the at least a portion of a hollow bore configured for attachment over an actuation unit of a drug delivery pen;
 a dosage sensor coupled to the primary module housing;
 a follower portion connected to the dosage sensor and disposed for movement relative to the primary module housing;
 retention forks connected to the follower portion, the retention forks configured to capture an actuation button of a drug delivery pen between the retention forks;
 a power source coupled to the primary module housing and spaced apart from the dosage sensor; and
 a microcontroller disposed proximate the primary module housing and electrically coupled to both the dosage sensor and the power source.

2. The medical module of claim 1, in which the secondary module housing comprises:
 first and second extensions that partially circumscribe the second longitudinal axis generally parallel to the first longitudinal axis.

3. The medical module of claim 2, in which each of the first and second extensions includes respective first and second locating tangs, each locating tang protruding beyond each extension.

4. The medical module of claim 3, in which the first locating tang is located at a position along the second longitudinal axis offset longitudinally with respect to the second locating tang.

5. The medical module of claim 2, in which each of the first and second extensions defines a generally circular cross-section of generally 30 degrees about the second longitudinal axis.

6. The medical module of claim 5, in which a portion of the secondary module housing circumscribes the second longitudinal axis to define a generally circular cross-section of generally 140 degrees about the longitudinal axis.

7. The medical module of claim 6, in which the portion of the secondary module housing is contiguous to both the first and second extensions to define a continuous surface that circumscribes generally 250 degrees about the second axis.

8. The medical module of claim 1, in which the dosage sensor includes a longitudinal member slidable along the longitudinal axis, the longitudinal member connected to a follower portion that extends from the primary module housing proximate the second module housing end.

9. The medical module of claim 8, in which the longitudinal member is configured for rotation about its axis.

10. The medical module of claim 1, in which the secondary module housing comprises a generally tubular extension circumscribing entirely the second longitudinal axis to define a hollow tubular member that extends along a length of the module housing.

11. The medical module of claim 1, in which the microcontroller comprises:
 a memory;
 a microprocessor coupled to the memory;
 an analog-to-digital converter coupled to the dosage sensor and the microprocessor so as to provide data on displacement of a follower portion; and
 a transceiver to transmit and receive data stored in memory.

12. The medical module of claim 1, in which the drug delivery pen comprises a disposable insulin pen.

13. The medical module of claim 1, in which the drug delivery pen comprises a reusable insulin pen.

14. The medical module of claim 1, in which the dosage sensor is selected from a group consisting of a rotary potentiometer, linear potentiometer, capacitive displacement sensor, optical displacement sensor, magnetic displacement sensor, encoder type displacement sensor, or combination thereof.

15. The medical module of claim 1, further comprising an inertial sensor disposed in the primary module housing to determine the orientation of the drug cartridge.

16. The medical module of claim 1, further comprising a micro switch to allow a determination of replacement of the drug delivery pen.

17. A medical communication unit comprising:
 a housing extending along a longitudinal axis from a first housing end to a second housing end to define at least a portion of a hollow bore in which the hollow bore is configured to couple over an actuation unit of a drug delivery pen;
 a casing connected to the housing and configured to enclose a portion of an outer surface of the housing, the casing being located asymmetrically with respect to the longitudinal axis to house electrical components;
 a dosage sensor disposed in the casing;
 a follower portion physically connected to the dosage sensor and disposed for movement relative to the housing; and
 a knob mounted to the housing and physically connected to the dosage sensor via slider fingers of the follower portion so that a portion of the dosage sensor is movable in proportion to movement of the knob along the longitudinal axis.

18. The medical module of claim 17, in which the dosage sensor includes a longitudinal member movable along the longitudinal axis, the longitudinal member connected to a follower portion that extends from the housing proximate the second housing end.

19. The medical module of claim 18, in which the longitudinal member comprises a slider disposed on a potentiometer, the slider being slidable on the potentiometer along the longitudinal axis between proximate the first housing end and the second housing end upon movement of the knob.

20. The medical module of claim 19, further comprising a switch disposed proximate the first housing end, the switch configured to respond as a momentary switch upon the knob being moved towards a terminal position proximate the second housing end.

21. The medical module of claim 17, in which the microcontroller comprises:
 a memory;
 a microprocessor coupled to the memory;
 an analog-to-digital converter coupled to the dosage sensor and the microprocessor so as to provide data on displacement of a follower portion; and
 a transmitter to transmit data stored in memory.

22. The medical module of claim 21, further comprising an inertial sensor disposed in the housing.

23. The medical module of claim 17, further comprising a micro switch disposed in the hollow bore to provide a signal to the microcontroller indicative of insertion and removal of a drug delivery pen.

24. The medical module of claim 17, in which the dosage sensor is selected from a group consisting of a rotary potentiometer, linear potentiometer, capacitive displacement sensor, optical displacement sensor, magnetic displacement sensor, encoder type displacement sensor, or combination thereof.

25. The medical module of claim 17, further comprising an inertial sensor disposed in the module housing to determine the orientation of the drug cartridge.

26. A dosage sensing module comprising:
 a housing extending along a longitudinal axis from a first housing end to a second housing end to define an internal surface of at least a portion of a hollow bore disposed about the longitudinal axis, the internal surface defining the hollow bore capable of completely enclosing a cylindrical outer surface of a portion of a drug delivery pen in one mode, and the internal surface of the hollow bore being visible to an observer in another mode when the housing is separated from the drug delivery pen; and
 means for measuring displacement of a dosage selector of the drug delivery pen.

* * * * *